United States Patent
Propheter et al.

(10) Patent No.: US 9,567,378 B2
(45) Date of Patent: Feb. 14, 2017

(54) IN SITU ORIENTED IMMOBILIZATION OF PROTEINS ON A SUPPORT

(75) Inventors: Daniel C. Propheter, El Dorado Hills, CA (US); Lara K. Mahal, South Orange, NJ (US)

(73) Assignee: New York University, New York, NY (US)

(*) Notice: Subject to any disclaimer, the term of this patent is extended or adjusted under 35 U.S.C. 154(b) by 1159 days.

(21) Appl. No.: 13/153,046

(22) Filed: Jun. 3, 2011

(65) Prior Publication Data

US 2011/0301057 A1    Dec. 8, 2011

Related U.S. Application Data

(60) Provisional application No. 61/351,192, filed on Jun. 3, 2010.

(51) Int. Cl.
C12M 3/00 (2006.01)
C07K 14/31 (2006.01)
C07K 1/107 (2006.01)

(52) U.S. Cl.
CPC ............. C07K 14/31 (2013.01); C07K 1/1077 (2013.01); C07B 2200/11 (2013.01)

(58) Field of Classification Search
None
See application file for complete search history.

(56) References Cited

U.S. PATENT DOCUMENTS

| | | | |
|---|---|---|---|
| 4,008,126 A | 2/1977 | Keyes | |
| 4,952,519 A | 8/1990 | Lau | |
| 6,288,037 B1* | 9/2001 | Talanian et al. | 514/20.1 |
| 2002/0058269 A1* | 5/2002 | Nock | C12N 15/1037 435/6.14 |
| 2002/0136726 A1* | 9/2002 | Anderson | A61K 47/48246 424/146.1 |
| 2002/0147996 A1* | 10/2002 | Benjamin | C07K 14/005 800/8 |
| 2002/0150968 A1* | 10/2002 | Wang | C12P 19/18 435/53 |
| 2003/0013130 A1* | 1/2003 | Charych | B01J 19/0046 435/7.1 |
| 2003/0059955 A1* | 3/2003 | Bamdad | B82Y 15/00 506/9 |
| 2003/0082560 A1 | 5/2003 | Wang | |
| 2003/0093226 A1* | 5/2003 | Ashby | G06F 19/22 702/20 |
| 2003/0180718 A1* | 9/2003 | Pillutla | C12N 15/1037 506/7 |
| 2004/0219693 A1* | 11/2004 | Camps | G01N 33/542 436/518 |
| 2005/0064510 A1* | 3/2005 | Akyuz | C07D 307/68 435/7.1 |
| 2006/0147943 A1* | 7/2006 | Lewis | G01N 33/54353 435/6.12 |
| 2006/0177451 A1* | 8/2006 | van den Oudenrijn | C07K 14/705 424/155.1 |
| 2007/0111253 A1* | 5/2007 | Harada | C07K 14/47 435/7.1 |
| 2007/0155013 A1* | 7/2007 | Akaike | C12N 5/0606 435/455 |
| 2008/0064025 A1* | 3/2008 | Su | G01N 33/542 435/5 |
| 2008/0268545 A1* | 10/2008 | Tajima | 436/94 |
| 2009/0176263 A1* | 7/2009 | Mandala | C07K 14/4722 435/15 |
| 2009/0325262 A1 | 12/2009 | Hodneland et al. | |
| 2014/0023591 A1* | 1/2014 | Sen Gupta | A61K 47/48815 424/9.6 |

OTHER PUBLICATIONS

Kuno et al., "Evanescent-Field Fluorescence-Assisted Lectin Microarray: A New Strategy for Glycan Profiling," Nature Meth. 2(11):851-856 (2005).
Pilobello et al., "Development of a Lectin Microarray for the Rapid Analysis of Protein Glycopatterns," ChemBioChem 6:1-4 (2005).
Clarizia et al., "Antibody Orientation Enhanced by Selective Polymer-Protein Noncovalent Interactions," Anal. Bioanal. Chem. 393:1531-1538 (2009).
Chen et al., "Fabrication of an Oriented Fc-Fused Lectin Microarray Through Boronate Formation," Angew. Chem. Int. Ed. 47:8627-8630 (2008).
Ha et al., "Oriented Immobilization of Antibodies with GST-Fused Multiple Fc-Specific B-Domains on a Gold Surface," Anal. Chem. 79(2):546-556 (2007).
Hsu et al., "A Simple Strategy for the Creation of a Recombinant Lectin Microarray," Mol. Biosyst. 4:654-662 (2008).
Propheter et al., "Fabrication of an Oriented Lectin Microarray," ChemBioChem 11:1203-1207 (2010).
Propheter et al., "Orientation of GST-Tagged Lectins via In Situ Surface Modification to Create an Expanded Lectin Microarray for Glycomic Analysis," Mol. BioSyst. 7:2114-2117 (2011).
International Search Report for International Patent Application No. PCT/US2011/039116 (Feb. 29, 2012).
Written Opinion of the International Searching Authority for International Patent Application No. PCT/US2011/039116 (Feb. 29, 2012).

* cited by examiner

*Primary Examiner* — Ann Lam
(74) *Attorney, Agent, or Firm* — LeClairRyan, a Professional Corporation

(57) ABSTRACT

The present invention relates to a method of directing in situ oriented immobilization of a protein on a support. This method involves providing a support and contacting the support with a solution. The solution comprises (a) a protein comprising a coupling moiety and (b) a molecule comprising a first group reactive with the support and a second group reactive with the coupling moiety. The molecule binds (i) the support at the first group and (ii) the coupling moiety at the second group, thereby immobilizing and orienting, in situ, the protein on the support. Also described are a protein array and a method of screening compounds for protein interaction.

17 Claims, 12 Drawing Sheets

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial
<220> FEATURE:
<223> OTHER INFORMATION: Primer

<400> SEQUENCE: 1
gacgacgaca agatgaaaga ggaaaccccg                                30

<210> SEQ ID NO 2
<211> LENGTH: 34
<212> TYPE: DNA
<213> ORGANISM: Artificial
<220> FEATURE:
<223> OTHER INFORMATION: Primer

<400> SEQUENCE: 2
gaggagaagc ccggtttaac cggcgaaacg aatg                           34

<210> SEQ ID NO 3
<211> LENGTH: 876
<212> TYPE: DNA
<213> ORGANISM: Artificial
<220> FEATURE:
<223> OTHER INFORMATION: Protein L gene fragment cloned into the pET-41
      vector

<400> SEQUENCE: 3
aaagaggaaa ccccggaaac acctgaaacc gattcggaag aagaagtgac gatcaaagcg      60
aacctgattt ttgccaatgg cagcacccaa acagcggaat tcaaaggcac cttcgagaaa    120
gcgacctctg aagcatatgc ctatgccgat acgctgaaaa aagacaacgg cgagtatacc    180
gtggatgtgg cggataaagg ttatacctg aacatcaaat ttgccggtaa agagaaaact     240
cctgaggagc cgaaagagga ggttaccatt aaagccaatc tgatctatgc cgacggaaaa    300
```

| | |
|---|---|
| acccagacgg cggagttcaa aggcacattc gaagaagcaa ctgccgaagc ttatcgttat | 360 |
| gctgatgccc tgaaaaaaga caatggcgag tatacggtgg acgttgccga caaaggctat | 420 |
| acgctgaaca tcaaattcgc tggtaaagag aaaaccccag aagaaccaaa agaggaggtt | 480 |
| acgatcaaag ccaacctgat ctatgccgat gggaaaacac aaacagctga gttcaaaggg | 540 |
| acgtttgagg aggctactgc tgaggcctat cgctatgccg acctgctggc taaagaaaac | 600 |
| gggaaatata cagtcgatgt ggccgacaaa ggttatacgc tgaacatcaa attcgccggt | 660 |
| aaagaaaaaa caccggagga gcctaaagaa gaagtcacca tcaaagccaa cctgatttat | 720 |
| gccgacggaa aaacacaaac tgccgagttc aaaggaacgt tgccgaagc gacggcggaa | 780 |
| gcatatcgct atgccgatct gctggccaaa gagaacggaa aatatacggc cgacctggaa | 840 |
| gatggaggtt atacaatcaa cattcgtttc gccggt | 876 |

<210> SEQ ID NO 4
<211> LENGTH: 1368
<212> TYPE: DNA
<213> ORGANISM: Artificial
<220> FEATURE:
<223> OTHER INFORMATION: Protein L gene synthesized by Genewiz

<400> SEQUENCE: 4

| | |
|---|---|
| atgaaaaaaa cggcgattgc tattgctgtg gctctggcag gatttgctac tgttgctcaa | 60 |
| gcggctgtcg aaaacaaaga ggaaaccccg aaaacacctg aaaccgattc ggaagaagaa | 120 |
| gtgacgatca aagcgaacct gattttgcc aatggcagca cccaaacagc ggaattcaaa | 180 |
| ggcaccttcg agaaagcgac ctctgaagca tatgcctatg ccgatacgct gaaaaaagac | 240 |
| aacggcgagt ataccgtgga tgtggcggat aaaggttata ccctgaacat caaatttgcc | 300 |
| ggtaaagaga aaactcctga ggagccgaaa gaggaggtta ccattaaagc caatctgatc | 360 |
| tatgccgacg gaaaaaccca gacggcggag ttcaaaggca cattcgaaga gcaactgcc | 420 |
| gaagcttatc gttatgctga tgccctgaaa aaagacaatg gcgagtatac ggtggacgtt | 480 |
| gccgacaaag gctatacgct gaacatcaaa ttcgctggta agagaaaaac cccagaagaa | 540 |
| ccaaaagagg aggttacgat caaagccaac ctgatctatg ccgatgggaa aacacaaaca | 600 |
| gctgagttca agggacgtt tgaggaggct actgctgagg cctatcgcta tgccgacctg | 660 |
| ctggctaaag aaaacgggaa atatacagtc gatgtggccg acaaaggtta tacgctgaac | 720 |
| atcaaattcg ccggtaaaga aaaaacaccg gaggagccta agaagaagt caccatcaaa | 780 |
| gccaacctga tttatgccga cggaaaaaca caaactgccg agttcaaagg aacgtttgcc | 840 |
| gaagcgacgg cggaagcata tcgctatgcc gatctgctgg ccaaagagaa cggaaaatat | 900 |
| acggccgacc tggaagatgg aggttataca atcaacattc gtttcgccgg taaaaaagtg | 960 |
| gacgagaaac cggaagaacc gatgacacac tataaactga ttctgaacgg aaaaacgctg | 1020 |
| aaaggcgaga caacaaccga agccgtggac gctgctactg ctgaaaaagt gttcaaacaa | 1080 |
| tatgccaacg acaacggtgt ggatggaaa tggacctatg acgatgccac caaaacattc | 1140 |
| acagtgaccg agaaaccaga agtcattgac gcctcggaac tgactccggc ggttacaaca | 1200 |
| tataaactgg tcattaacgg aaaaaccctg aaaggcgaga ctaccacaaa agcggtagac | 1260 |
| gctgaaacag cggagaaagc attcaaacaa tatgccaatg ataatggcgt tgacggcgtt | 1320 |
| tggacatatg acgacgctac gaaaaccttc acggtgacgg aaatgtaa | 1368 |

IN SITU ORIENTED IMMOBILIZATION OF PROTEINS ON A SUPPORT

This application claims the benefit of U.S. Provisional Patent Application Ser. No. 61/351,192, filed Jun. 3, 2010, which is hereby incorporated by reference in its entirety.

This invention was made with government support under National Science Foundation Career Grant No. CHE-0644530. The government has certain rights in the invention.

FIELD OF THE INVENTION

This invention relates to in situ oriented immobilization of proteins on a support.

BACKGROUND OF THE INVENTION

Protein microarrays are important tools for the discovery of biomarkers, protein-protein interactions, and protein-glycan interactions (MacBeath, "Protein Microarrays and Proteomics," *Nat. Genetics* 32:526-32 (2002); Krishnamoorthy et al., "Glycomic Analysis: An Array of Technologies," *ACS Chem. Biol.* 4(9):715-32 (2009)). Lectin microarrays are protein microarrays for the detection and analysis of cellular glycosylation (Pilobello et al., "A Ratiometric Lectin Microarray Approach to Analysis of the Dynamic Mammalian Glycome," *Proc. Natl. Acad. Sci. U.S.A.* 104(28):11534-9 (2007); Pilobello et al., "Development of a Lectin Microarray for the Rapid Analysis of Protein Glycopatterns," *Chembiochem* 6(6):985-9 (2005)).

The current approach of creating lectin microarrays is limited, in part, by glycan-detecting sensitivity as a function of protein concentration. Recently, a method to utilize bacterial lectins for glycomic analysis has been developed (Hsu et al., "A Simple Strategy for the Creation of a Recombinant Lectin Microarray," *Mol. Biosyst.* 4(6):654-62 (2008)). These lectins are recombinantly expressed as fusion proteins containing an N-terminal glutathione-S-transferase-("GST"-) and a polyhistidine-("His6"-) tag. Previous studies have shown that GST-fusion proteins can be oriented on a glutathione ("GSH") surface. Orienting lectins using the GST-GSH interaction on glutathione-treated slides was found to have a significant (>2-fold) increase in their activity. Although this was beneficial for a recombinant lectin microarray, a solely recombinant array means a significant loss of diversity in binding proteins on an array. Thus, one drawback of this approach is the requirement that all proteins to be displayed on the array have a GST-moiety. This means that only recombinant proteins can be utilized on a single array. It would be useful to also employ lectins (or other proteins) from natural (non-recombinant) sources.

In one approach, two distinct surfaces were created in a single subarray, displaying the benefits of orienting recombinant lectins which increased the sensitivity of the lectins to detect in the nanomolar (nM) concentration of glycoprotein (Propheter et al., "Fabrication of an Oriented Lectin Microarray" *Chembiochem. May* 18, 2010). This, compared to other methods of detection (such as evanescent wave detection), proved simple and inexpensive. The creation of a dual-surface array was also cost-effective. However, available probes are limited to recombinant lectins currently available. In the search for a methodology for the inclusion of oriented lectins to the standard microarray in which a single slide surface chemistry is utilized, a practical approach that is neither tedious nor expensive and is widely applicable to similar systems is needed.

The activity of proteins in protein microarrays is always a concern. For example, the random coupling of proteins via amide coupling chemistry to lysine residues often impinges upon protein activity, causing occlusion of active sites and in some cases denaturation of the protein structure. Control over the orientation of proteins is an important factor in enhancing activity on a solid support. However, in arrays, often there is also a desire to maximize the number of probes to be utilized. Thus, the limitations inherent in a recombinant array, i.e., that every protein has to be expressed with the same tag to be bound to a uniform surface, is undesirable if arrays that include proteins from a wide variety of sources are desired. Creating surfaces that can accommodate both recombinant and untagged proteins would enhance the utility and activity of current protein arrays.

The present invention is directed to overcoming these and other limitations in the art.

SUMMARY OF THE INVENTION

One aspect of the present invention relates to a method of directing in situ oriented immobilization of a protein on a support. This method involves providing a support and contacting the support with a solution. The solution comprises (a) a protein comprising a coupling moiety and (b) a molecule comprising a first group reactive with the support and a second group reactive with the coupling moiety. The molecule binds (i) the support at the first group and (ii) the coupling moiety at the second group, thereby immobilizing and orienting, in situ, the protein on the support.

Another aspect of the present invention is directed to a protein array including a first protein immobilized at a first location on a support surface in an oriented manner. The first protein is immobilized on the surface via a molecule comprising (i) a first group reactive with the protein and (ii) a second group reactive with the surface. A second protein is immobilized at a second location on the surface. The surface has a homogenous chemistry reactive with both the molecule at the second group and the second protein.

A further aspect of the present invention is directed to a method of screening compounds for protein interaction. This method involves providing a protein array according to the present invention, contacting the array with compounds to be screened, and detecting compounds that interact with the first and/or second protein, thereby screening compounds for protein interaction.

The present invention relates to in situ modification of a surface to orient proteins concomitant with spotting. This technique allows one to retain the advantages of the orientation of proteins while also allowing both recombinant and native proteins to be displayed in the same array. The method is applicable to current sets of recombinant lectins (and other types of proteins) and the vast potential of future additions of GST-fusion lectins (and other types of proteins), without the loss of diversity inherent in proteins from multiple sources.

BRIEF DESCRIPTION OF THE DRAWINGS

FIG. 7A is a schematic illustration of in situ oriented GST-PpL binding to the κ light chains of IgM-FITC. FIG. 7B represents GST-fusion proteins (0.5 mg/mL) that were printed in GSH-B and probed for activity against IgM-FITC (1.5 μg/mL). Graphical representations are representative of triplicate arrays. Error bars indicate standard deviations from the median value.

FIG. 9A illustrates the result of CA19-9 (0.25 mg/mL) that was printed under various conditions with or without GST-PpL (0.25 mg/mL) in GSH-B and PB. When printed in situ with GST-PpL, CA19-9 displays ~8-fold increase in activity at 2 μM Sialyl Lewis$^a$-Cy3. FIG. 9B is a graphical representation of the data shown in FIG. 9A. In situ oriented CA19-9 displayed a 5-fold increase in detection limits over the non-oriented antibody (25.6 pM versus 128 pM). Graphs are representative of duplicate arrays and error bars indicate standard deviations from the median value.

FIG. 11A is a graphical representation of the deposition of IgM-Cy5. IgM-Cy5 (0.25 mg/mL) was printed in either GSH-B or PB and with or without GST-PpL (0.02 mg/mL). Absolute fluorescence of IgM-Cy5 was observed through the Cy5 channel. There is ~50% less IgM-Cy5 when oriented in situ (IgM+PpL+GSH-B) than when printed under standard print conditions (IgM+PB). FIG. 11B is a graphical representation of the detection of displayed IgM-Cy5 as observed after incubation with goat α-mu chain-Cy3 (1 μg/mL). Observation through the Cy3 channel shows that oriented antibody is ~2.5× better detected than non-oriented, or randomly deposited, antibody. FIG. 11C is a visual representation of data shown in FIGS. 11A and 11B in Cy5, Cy3, and Cy5:Cy3 ratiometric channels. Graphs are representative of triplicate arrays and error bars indicate standard deviations from the median value.

DETAILED DESCRIPTION OF THE INVENTION

Figure 1:
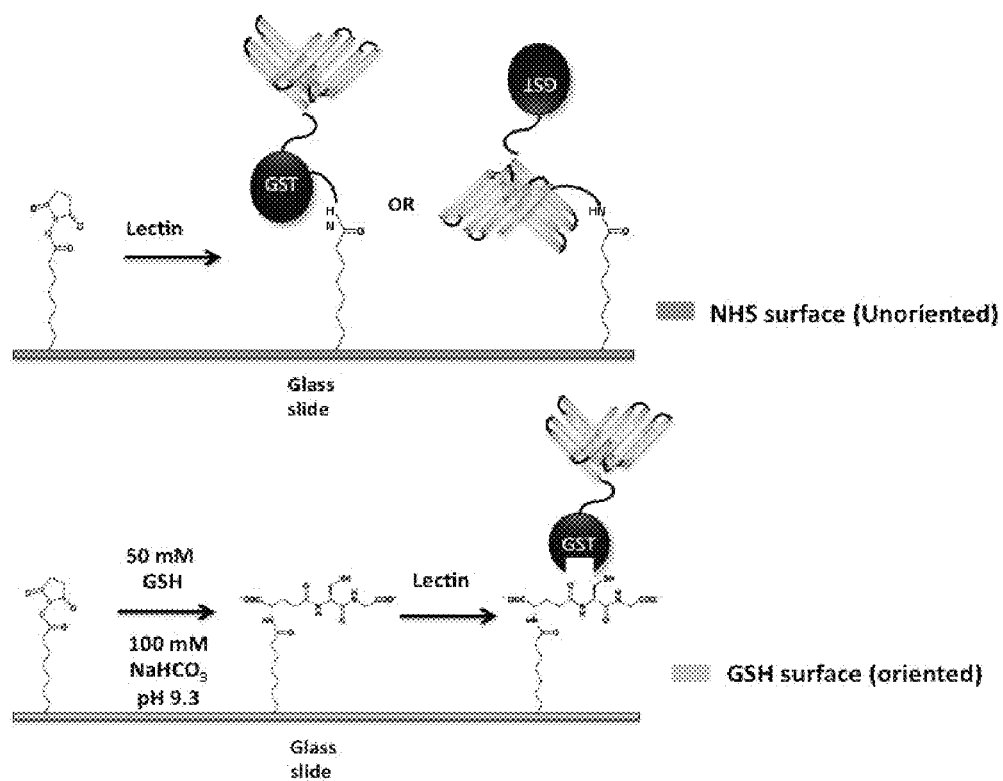
FIG. 1 is a schematic illustration showing how GST-tagged lectins can be attached to a surface in either an unoriented (via an amide bond) or oriented (via a specific GST-GSH interaction) manner.

One aspect of the present invention relates to a method of directing in situ oriented immobilization of a protein on a support. This method involves providing a support and contacting the support with a solution. The solution comprises (a) a protein comprising a coupling moiety and (b) a molecule comprising a first group reactive with the support and a second group reactive with the coupling moiety. The molecule binds (i) the support at the first group and (ii) the coupling moiety at the second group, thereby immobilizing and orienting, in situ, the protein on the support.

According to this method of the present invention, a support is provided upon which a protein can be immobilized. Suitable supports include anything having a surface upon which it may be desirable, pursuant to the method of the present invention, to direct in situ oriented immobilization of a protein. The support may be either organic or inorganic, biological or non-biological, or any combination of these materials. The support can comprise, for example, a material selected from silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for supports pursuant to this method of the present invention. In addition, ceramics and polymers may also be used as supports. Polymers which may be used as support materials include, but are not limited to, the following: polystyrene; poly(tetra) fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polycatides; polymethacrylimide (PMI); polyalkenesulfone (PAS); polypropylene; polyethylene; polyhydroxyethylmethacrylate (HEMA); polydimethylsiloxane; polyacrylamide; polymide; and block-copolymers. Preferred supports of the present invention include silicon, silica, glass, and polymers. Supports for use in the present invention may be a combination of any of the aforementioned support materials.

In one embodiment, the support is a microarray support. The surface of the support may be flat and firm or semi-firm. Alternatively, the surface of the support need not necessarily be flat or entirely two-dimensional. Significant topological features may be present on the support surface. For instance, walls or other barriers may separate discrete locations on the support. Similarly, the support may have wells or discrete locations of indentations. In one embodiment, the support is a filter membrane. In another embodiment, the support is transparent or translucent.

While the support may have a surface that has regions of different chemistry, according to one embodiment, the support has a surface with a homogenous chemistry. In other words, according to this embodiment, the chemistry of the surface of the support onto which proteins are immobilized pursuant to the method of the present invention is uniform across the entire surface prior to contacting the support with the solution. In another embodiment, the support may contain, for example, a coating on the support, where the coating provides a functional and uniform surface chemistry. Such a coating may either be formed on the support surface or applied to the support surface. Thus, when it is said that a protein is immobilized on a support, this can mean that a protein is immobilized on the surface chemistry of the support.

In other embodiments, the support has a surface coating that is optionally a metal film. Suitable metal films for protein microarrays are known and may include aluminum, chromium, titanium, tantalum, nickel, stainless steel, zinc, lead, iron, copper, magnesium, manganese, cadmium, tungsten, cobalt, and alloys or oxides thereof. In one embodiment, the metal film is a noble metal film. Noble metals that may be used for a support surface coating may include, for example, gold, platinum, silver, and/or copper. Electron-beam evaporation may be used to provide a thin coating of gold on the surface of the support. Metal films can be coated to provide the specific desired chemistry for a particular use.

In one embodiment, the support has a surface chemistry comprising N-Hydroxysuccinimide ("NHS"). In another embodiment, the support has a surface chemistry comprising an epoxide. Other surface chemistries are also suitable and may include, for example, the following compounds and/or functional groups: maleimide, sulfhydryl, amide coupling from activated esters, carboxylic acid, amine, aldheyde, ketone, hydrazide, hydroxylamine, α-halocarbonyl, aryl halide, alkyl halide, azide, alkyne, cyclooctyne, cyclyooctene, tetrazine, diene, alkene (for Diels-Alder reactions), and diaryltetrazole.

According to the method of the present invention, the support is contacted with a solution comprising (a) a protein comprising a coupling moiety and (b) a molecule comprising a first group reactive with the support and a second group reactive with the coupling moiety.

Solutions of the present invention include solutions suitable for spotting, printing, depositing, etc., onto a support in a manner that a protein contained in the solution is capable of being immobilized on the support, in situ, in an oriented manner. In one embodiment, the molecule (comprising the first and second group) is present in the solution at a molar concentration that is higher than that of the coupling moiety of the protein. While the molecule may potentially bind the coupling moiety in the solution, this reaction is, in one embodiment, labile. Accordingly, when the solution comes into contact with the support, binding of the protein directly to the support (or surface chemistry thereof) cannot compete with the higher concentration of molecule in the solution. Thus, the molecule outcompetes the protein for binding to the support (or surface chemistry thereof), causing the protein to bind at its coupling moiety to the second group of the molecule (rather than the support, or surface chemistry thereof, directly), thereby immobilizing, in an in situ oriented manner, the protein on the support.

In another embodiment of the solution, orthogonal covalent chemistry could be used if the kinetics of the reaction were fast. For example, orthogonal covalent chemistry could be used in situations where the protein is not a fusion protein that does not have a traditional affinity tag (e.g., $His_6$, GST, or MBP), but instead has been engineered to contain an unnatural amino acid with a specific functional group (i.e., an azide, alkyne, aldehyde, etc.). According to this embodiment, the molecule itself contains two different functional groups: one that reacts with the support and one that interacts with the fusion protein.

In yet another embodiment of the solution, a polyvalent molecule with multiple linker small molecules on a single scaffold typically shows greater affinity toward its targets. See, e.g., Huang et al., "Tris-Nitriloacetic Acids of Subnanomolar Affinity Toward Hexahistidine Tagged Molecules," *Bioconjugate Chemistry* 20:1667-72 (2009), which is hereby incorporated by reference in its entirety. According to this embodiment, the polyvalent molecule would then act as the molecule (comprising reactive groups) which would have a greater affinity for the protein, so that excess amounts are not necessary in the solution to orient the protein on the support.

In one embodiment, the solution is a sodium borate buffer solution. The sodium borate buffer used is based on the protocol for blocking NHS-activated slides (SCHOTT North America, Inc., Elmsford, N.Y.), which uses 50 mM sodium borate at pH 8.5. Other sodium borate concentrations used have been up to 100 mM and down to 25 mM, with a pH range from about 8.0-8.7. Other buffers include phosphate buffered saline (PBS) from 100 to 10 mM sodium phosphate, pH 6.5-7.8, and sodium bicarbonate up to 100 mM concentration and pH 9.0-9.5. The protein solutions are initially mixed at room temperature, but are stored (prior to printing) and during the print are kept at 4-8° C. The extended protein coupling after print completion occurs at room temperature. Typically, more basic solutions are more amenable to amine coupling reactions, but the more extreme the pH from neutral buffer, the more denaturation and aggregation of the protein may occur.

The solution contains a protein comprising a coupling moiety, preferably located at the N-terminal region of the protein or the C-terminal region of the protein. Proteins of the solution, which are suitable for immobilization on the support according to the method of the present invention, may be any protein, protein fragment, polypeptide, or amino acid chain. The coupling moiety may be a portion of a native protein or added to a protein via, e.g., recombinant expression as described infra.

In one embodiment, the protein is a protein capture agent that can interact with proteins in high affinity and high specificity. According to this embodiment, it is typically desirable to have an affinity binding constant ($K_d$) between a protein capture agent and target molecule in ranges from low µM to nM for, e.g., glutathione and GST (Fabrini et al., "Monomer-Dimer Equilibrium in Glutathione Transferases: A Critical Re-Examination," *Biochemistry* 48(43):10473-82 (2009), which is hereby incorporated by reference in its entirety). In the case of, e.g., the maltose-binding protein and maltose, the affinity binding constant may be in a range of about 1.2-0.66 µM (Telmer et al., "Insights Into the Conformational Equilibria of Maltose-Binding Protein by Analysis of High Affinity Mutants," *J. Biol. Chem.* 278(36): 34555-67 (2003), which is hereby incorporated by reference in its entirety). By way of another example, Huang et al., "Tris-Nitriloacetic Acids of Subnanomolar Affinity Toward Hexahistidine Tagged Molecules," *Bioconjugate Chemistry* 20:1667-72 (2009), which is hereby incorporated by reference in its entirety, discusses Ni-NTA (~10 µM) and a production of a multivalent NTA-containing compound with ~10 nM affinity. There are several classes of molecules that can be used as protein capture agents. For example, antibodies are a class of naturally occurring protein molecules that are capable of binding targets with high affinity and specificity. The properties and protocols of using antibody can be found in USING ANTIBODIES; A LABORATORY MANUAL (Cold Spring Harbor Laboratory Press, by Ed Harlow and David Lane, Cold Spring Harbor, N.Y. 1999), which is hereby incorporated by reference in its entirety. Antigens can also be used as protein capture agents if antibodies are intended targets for detection. Protein scaffolds such as whole protein/enzyme or their fragments can be used as protein capture agents as well. Examples include phosphotases, kinases, proteases, oxidases, hydrolyases, cytokines, or synthetic peptides.

In a particular embodiment of the present invention, the protein is a lectin protein.

Proteins for the solution may be native proteins, i.e., proteins found in and isolated from living organisms and/or tissues. Suitable proteins may also include recombinant proteins or proteins that do not occur without recombinant manipulation. Thus, proteins for immobilization on a support pursuant to the method of the present invention may be isolated from a variety of organisms and/or tissues or cells or produced by any of the variety of means known to those of ordinary skill in the art. The protein may be naturally occurring and obtained by purification, or may be non-naturally occurring and obtained by synthesis. Proteins, enzymes, antibodies, peptides, peptidomimetic compounds, polypeptides, fragments or derivatives, fusion proteins, etc., may be obtained, when available, from commercial sources, such as Sigma (U.S.A.). Methodologies for synthesizing (for example, using cDNA expression libraries or chemical synthesis of polypeptides followed by refolding into native proteins) or otherwise obtaining the protein for use in the present invention are well-known.

Recombinant proteins can be expressed from recombinant DNA either in vivo or in vitro. Generally, recombinant expression of proteins involves inserting a DNA molecule encoding the desired protein into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the protein and a transcription termination (i.e., polyadenylation sequence) can be operably coupled 3' thereof.

Polynucleotides encoding a desired protein can be inserted into an expression system or vector to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18, or pBR322 may be used. When using insect host cells, appropriate transfer vectors compatible with insect host cells include, pVL1392, pVL1393, pAcGP67, and pAcSecG2T, which incorporate a secretory signal fused to the desired protein, and pAcGHLT and pAcHLT, which contain GST and 6×His tags (BD Biosciences, Franklin Lakes, N.J.). Suitable viral vectors include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) and subsequently the amount of desired protein that is produced and expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. The promoters can be constitutive or, alternatively, tissue-specific or inducible.

According to one embodiment, the protein is a fusion protein containing a protein and a coupling moiety not native to the protein. In this embodiment, the coupling moiety may be located at either the N-terminal region or the C-terminal region of the protein. In one embodiment, the coupling moiety is located at the N-terminal region.

In another embodiment of the present invention, the protein comprises a polyhistidine tag, which binds to a $Ni^{2+}$ immobilized with NTA which are covalently linked to beads or slides (Waugh, "Making the Most of Affinity Tags," *Trends in Biotech.* 23(6):316-20 (2005), which is hereby incorporated by reference in its entirety).

The solution also contains a molecule comprising a first group reactive with the support and a second group reactive with the coupling moiety. The molecule binds (i) the support at the first group and (ii) the coupling moiety at the second group, thereby immobilizing and orienting, in situ, the protein on the support.

Suitable molecules are those having first and second reactive groups specific to the moiety and surface chemistry of a particular support. In other words, the molecule may be chosen based on its reactivity to the protein in the solution and the surface chemistry of the support. Specific examples are described infra.

According to one embodiment of the present invention, the solution contains a recombinant fusion protein having, as a coupling moiety, glutathione-S-transferase (GST). The coupling moiety GST is a common protein scaffold present in many commercially available DNA vectors, and is more commonly used as a way of purifying GST-fusion proteins out of a cell lysate by taking advantage of the strong non-covalent interaction between glutathione (GSH) and GST. In this specific embodiment, the molecule in the solution, which has a first group reactive with the support and a second group reactive with the coupling moiety, is glutathione. When brought into contact with a support having a surface chemistry of NHS, GSH reacts with the NHS surface chemistry of the support, thereby binding the support, and also reacts with the coupling moiety thereby immobilizing and orienting, in situ, the protein on the support. The mechanism of in situ oriented immobilization according to this embodiment of the present invention is illustrated in the scheme of FIG. 1. Specifically, GST-tagged lectins can be attached to the surface of a support in either an unoriented (via an amide bond) or oriented (via a specific GST-GSH interaction) manner. The present invention relates to a method in which proteins (such as lectins) are immobilized to a support in an oriented manner. Accordingly, one embodiment of the present invention is focused on the GST-GSH interaction as a way to immobilize and orient GST-fusion proteins, with emphasis on lectins, thereby increasing the binding activity of the protein via orientation.

Other combinations of proteins, coupling moieties, molecules, and support chemistries can also be used to direct in situ oriented immobilization of proteins pursuant to the method of the present invention. By way of example, suitable coupling pairs include, without limitation, maltose-binding protein and maltose, and $His_6$ and $Ni^{2+}$-NTA. Other examples can be found in Waugh, "Making the Most of Affinity Tags," *Trends in Biotech.* 23(6):316-20 (2005), which is hereby incorporated by reference in its entirety. Other affinity tags are the N-utilization sequence A (NusA), the FLAG and BAP tags, streptavidin- and calmoldulin-binding peptides, and the S tag. These affinity tags tend to be less used due to the cost of the reagents.

Pursuant to the method of the present invention, proteins are immobilized on the support in an oriented manner. For purposes of the present invention, an "oriented" protein is a protein immobilized on the support in an orientation that is beneficial for the specific purposes for which the protein is immobilized on the support. For example, if the protein is immobilized on the support for use as a capture probe, then an "oriented" protein is immobilized in a way to, e.g., maximize the possibility of capture with a protein from a capture solution. In another example, the protein is a lectin and the lectin is oriented on the support in a manner to increase accessibility of the lectin's carbohydrate-binding site. In one embodiment, immobilizing a protein on a support in an oriented manner is achieved via use of a molecule that binds both the support (or its surface chemistry) and a coupling moiety of the protein. By this means, the protein takes on a particular conformation and or position relative to the support.

While the solution contains a protein comprising a coupling moiety, other proteins not having a coupling moiety that reacts with the molecule in the solution may also be present in the solution. According to this embodiment, the solution contains proteins comprising a coupling moiety that require the second group of the molecule reactive with the coupling moiety to immobilize the protein on the support. The other proteins in the solution, which do not have a coupling moiety reactive with the molecule, are capable of being immobilized on the support without reacting with the molecule, because they are reactive directly with the support (or its surface chemistry). Thus, the molecule contained in the solution does not necessarily bind every protein also contained in the solution. According to this embodiment, recombinant proteins and native proteins can exist in the same solution and can be immobilized on the support at separate and discrete locations, but only the recombinant proteins, or those proteins containing a coupling moiety reactive with the molecule, are immobilized in an oriented manner.

In one embodiment, the method of directing in situ oriented immobilization of a protein on a support is carried out to provide a protein microarray. In practice, a protein microarray is brought into contact with a biological fluid sample and proteins in the sample will adsorb to both areas spotted with specific protein capture agents and areas without protein capture agents. Since a protein microarray is intended to be used for the measurement of specific interactions between protein capture agents on the support with certain proteins or other molecules in a biological fluid sample, the non-specific binding of sample proteins to non-spotted areas would give rise to high background noise. The term non-specific binding refers to the tendency of protein molecules to adhere to a solid surface in a non-selective manner. This high background noise resulting from the non-specific binding will interfere with reporter signals to be detected from the spotted area unless the non-specific binding is blocked in an appropriate manner. Typically, the protein microarray will be immersed in a solution containing a blocking agent to block the non-specific binding sites before its contact with the intended analyte solution. A commonly used method for blocking protein non-specific binding is to treat the surface of the substrate with a large excess of bovine serum albumin. The non-spotted surface area may also be chemically modified with polyethylene glycol (PEG), phospholipid, or poly lysine to prevent non-specific binding.

When employed to produce a protein microarray, contacting the support with the solution can be carried out at different specified locations or on separate patches of an array. Typically, the protein arrays comprise micrometer-scale, two dimensional patterns of locations or patches of proteins immobilized on the surface of a support. A variety of techniques may be used to bring the solution in contact with the surface of the support. These techniques are well known to those skilled in the art and will vary depending upon the desired use. For example, two types of ways people manufacture protein microarrays are through contact and non-contact printers. In contact printing, the pin dips into a protein solution and picks up the solution into the pin tip via capillary action, and then the pin will make direct contact with the slide. In non-contact printing, the microarrayer uses a piezo electric pin head that deposits the protein solution. The piezo pin will actively take up the protein solution (as opposed to inactive, capillary action) and then eject the solution onto the support. For non-contact printing, SMP3 pins (from Telechem Int'l., Inc., Sunnyvale, Calif.) may be used, although other types of pins are available and differ in spot size and how much solution is wicked up into the pin tip. The same holds true for the pins for contact printing. One example is the Nanoplotter II (from GeSiM, Dresden, Germany) and the associated nanotip and picotip pins. Other contact and non-contact printers are available from a wide number of companies.

In another embodiment of the present invention, the solution comprises an antibody to which the protein binds, and said method is carried out to direct in situ oriented immobilization of an antibody on a support.

Production of antibodies that can be used as the proteins pursuant to the present invention can be produced by well-known procedures. In particular, polyclonal antibodies and fragments thereof can be raised according to known methods by administering the appropriate antigen or epitope to a host animal selected, e.g., from pigs, cows, horses, rabbits, goats, sheep, and mice, among others, and then recovering serum (containing the antibodies) from the host animal. Various adjuvants known in the art can be used to enhance antibody production.

Monoclonal antibodies can be prepared using hybridoma methods, such as those described by Kohler and Milstein, "Continuous Cultures of Fused Cells Secreting Antibody of Predefined Specificity," *Nature* 256:495-7 (1975), which is hereby incorporated by reference in its entirety. Using the hybridoma method, a host animal is immunized to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce the desired monoclonal antibodies can be determined by immunoprecipitation, immunoblotting, or by an in vitro binding assay such as radioimmunoassay (RIA) or enzyme-linked immunosorbent assay (ELISA) and can then be propagated either in in vitro culture using standard methods (JAMES W. GODING, MONOCLONAL ANTIBODIES: PRINCIPLES AND PRACTICE (Academic Press 1986), which is hereby incorporated by reference in its entirety) or in vivo as ascites tumors in an animal. The monoclonal antibodies can then be purified from the culture medium or ascites fluid.

Alternatively, monoclonal antibodies can also be made using recombinant DNA methods as described in U.S. Pat. No. 4,816,567 to Cabilly et al., which is hereby incorporated by reference in its entirety. Polynucleotides encoding a monoclonal antibody are isolated from mature B-cells or hybridoma cells by RT-PCR using oligonucleotide primers that specifically amplify the genes encoding the heavy and light chains of the antibody. The isolated polynucleotides encoding the heavy and light chains are then cloned into suitable expression vectors, which when transfected into host cells, monoclonal antibodies are generated by the host cells. Also, recombinant monoclonal antibodies or fragments thereof of the desired species can be isolated from phage display libraries as described (McCafferty et al., "Phage Antibodies: Filamentous Phage Displaying Antibody Variable Domains," *Nature* 348:552-554 (1990); Clackson et al., "Making Antibody Fragments Using Phage Display Libraries," *Nature,* 352:624-628 (1991); and Marks et al., "By-passing Immunization: Human Antibodies from V-gene Libraries Displayed on Phage," *J. Mol. Biol.* 222:581-597 (1991), which are hereby incorporated by reference in their entirety).

In addition to utilizing whole antibodies, the methods of the present invention encompass use of binding portions of such antibodies. Such binding portions include Fab fragments, $F(ab)_2$ fragments, Fab' fragments, $F(ab')_2$ fragments, Fd fragments, Fd' fragments, Fv fragments, and minibodies, e.g., 61-residue subdomains of the antibody heavy-chain variable domain (Pessi et al., "A Designed Metal-binding Protein with a Novel Fold," *Nature* 362:367-369 (1993), which is hereby incorporated by reference in its entirety). Domain antibodies (dAbs) (see, e.g., Holt et al., "Domain Antibodies: Proteins for Therapy," *Trends Biotechnol.* 21:484-90 (2003), which is hereby incorporated by reference in its entirety) may also be suitable for the methods of the present invention. These antibody fragments can be made by conventional procedures, such as proteolytic fragmentation procedures, as described in J. Goding, MONOCLONAL ANTIBODIES: PRINCIPLES AND PRACTICE 98-118 (1984), which is hereby incorporated by reference in its entirety.

Further, single chain antibodies may also be suitable for the present invention (See e.g., U.S. Pat. No. 5,476,786 to Huston and U.S. Pat. No. 5,132,405 to Huston & Oppermann; Huston et al., "Protein Engineering of Antibody Binding Sites: Recovery of Specific Activity in an Anti-digoxin Single-chain Fv Analogue Produced in *Escherichia coli,*" *Proc. Nat'l Acad. Sci. USA* 85:5879-83 (1988); U.S. Pat. No. 4,946,778 to Ladner et al.; Bird et al., "Single-chain Antigen-binding Proteins," *Science* 242:423-6 (1988); Ward et al., "Binding Activities of a Repertoire of Single Immunoglobulin Variable Domains Secreted from *Escherichia coli,*" *Nature* 341:544-6 (1989), which are hereby incorporated by reference in their entirety). Single chain antibodies are formed by linking the heavy and light immunoglobulin chain fragments of the Fv region via an amino acid bridge, resulting in a single chain polypeptide.

Figure 6:
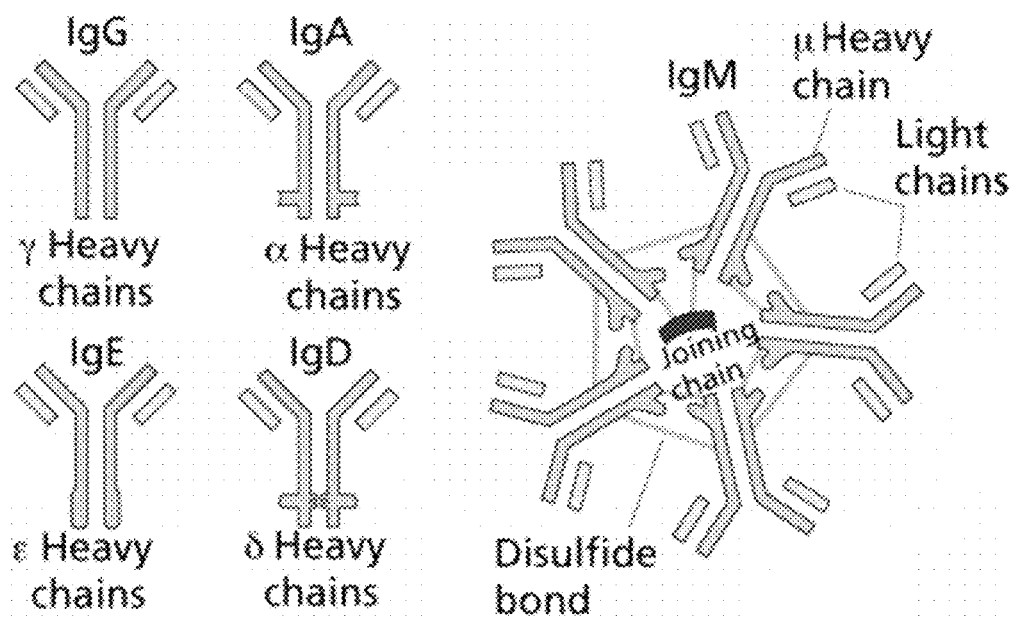
FIG. 6 is a schematic illustration showing the structures of common antibody isotypes. IgG, IgE, and IgD antibodies are monomeric in nature with an easily accessible Fc domain. IgA and IgM antibodies are multi-meric bound via protein complexes near the Fc domains, making those domains less accessible.

In one embodiment, the general strategy of orienting GST-fusion proteins on an in situ modified solid support, as described herein, is adapted to perform a one-pot orientation of untagged IgG antibodies via GST-fusion proteins of Protein A (SpA) and Protein G (SpG), which bind to the Fc domains of antibodies. Other fusion proteins now known or later discovered that bind antibodies may also be used in the methods of the present invention. IgG antibodies are monomeric, but IgM and IgA are pentameric and dimeric, respectively, as shown in FIG. 6. In one embodiment of the present invention, the antibody is IgG, or a fragment thereof. In an alternative embodiment, the antibody is a multivalent antibody selected from IgM and IgA, or a fragment thereof. These multimeric antibodies are bound together via the Fc domains, thus complicating the orientation strategy of the GST-SpA and -SpG proteins. Aside from these well-characterized SpA and SpG antibody-binding proteins, another protein from *Peptostreptococcus magnus,* PpL, also binds to light-chain fragments of antibodies with kappa (κ) light chains.

In one embodiment of the present invention, the protein comprises Protein A (SpA), Protein G (SpG), or a fragment thereof. In an alternative embodiment, the protein is *Peptostreptococcus magnus* PpL. In mammals, only lambda (λ)

and κ light chains are present on antibodies, and of the mammals, only mouse, rat, rabbit, and humans are known to contain protein L-binding κ chains. Ideally, a GST-PpL fusion protein would bind to a κ chain fragment from a multivalent antibody and become oriented upon printing in a GSH-containing buffer. In one embodiment, the protein binds the antibody via an Fc domain. In another embodiment, the *Peptostreptococcus magnus* PpL binds the antibody at a light chain fragment of the antibody.

The method of the present invention may be carried out to create, for example, bio sensors, micromachined devices, and diagnostic devices, which may be suited for use in, e.g., drug development, medical diagnostics, proteomics, and biosensor applications.

Another aspect of the present invention is directed to a protein array comprising a first protein immobilized at a first location on a support surface in an oriented manner. The first protein is immobilized on the surface via a molecule comprising (i) a first group reactive with the protein and (ii) a second group reactive with the surface. A second protein is immobilized at a second location on the surface. The surface has a homogenous chemistry reactive with both the molecule at the second group and the second protein.

In some cases, the protein array of the present invention will comprise at least about ten discrete locations or spots on the support where the solution is in contact with the support and a protein of a solution is immobilized on the support. In another embodiment, the array comprises at least about 50 discrete locations. In yet another embodiment the array comprises at least about 100 discrete locations of immobilized protein. In still another embodiment, the array of proteins may comprise more than $10^3$, $10^4$, or $10^5$ patchesor discrete locations.

The area of surface of the support covered by each of the discrete locations where the solution contacts the support is preferably no more than about 0.25 mm$^2$. In one embodiment, the area of the support covered by each of the solution spots is between about 1 μm$^2$ and about 10,000 μm$^2$. In another embodiment, each spot covers an area of the substrate surface from about 100 μm$^2$ to about 2,500 μm$^2$. In an alternative embodiment, a spot may cover an area of the support surface as small as about 2,500 nm$^2$, although spots of such small size are generally not necessary for the use of the array.

Spots where the solution contacts the surface of a support may be of any geometric shape. For instance, the spots may be rectangular or circular. The spots of the array may also be irregularly shaped.

The distance separating the spots on the support where the solution is in contact with the surface of the support can vary. Preferably, the spots of the array are separated from neighboring spots by about 1 μm to about 500 μm. Typically, the distance separating the spots is roughly proportional to the diameter or side length of the spots on the array if the spots have dimensions greater than about 10 μm. If the spot size is smaller, then the distance separating the spot will typically be larger than the dimensions of the spot.

In one embodiment, spots where the solution contacts the support are all contained within an area of about 1 cm$^2$ or less on the surface of the support. In one embodiment, therefore, the support comprises 100 or more spots within a total area of about 1 cm$^2$ or less on the surface of the support. Alternatively, an array comprises $10^3$ or more spots within a total area of about 1 cm$^2$ or less. In other embodiments of the invention, all of the spots of the array are contained within an area of about 1 mm$^2$ or less on the surface of the support.

Typically, only one type of protein is immobilized on each spot of an array. In one embodiment, the protein immobilized on one spot differs from the protein immobilized on a second spot of the same array. In such an embodiment, a plurality of different proteins are present on separate spots of the array.

In one embodiment, each of the spots of the array comprises a different protein. For instance, an array comprising about 100 spots could comprise about 100 different proteins. Likewise, an array of about 10,000 spots could comprise about 10,000 different proteins. In an alternative embodiment, however, each different protein is immobilized on more than one separate spot on the array. For instance, each different protein may optionally be present on two to six different spots.

This aspect of the present invention is carried out with regard to the embodiments described above.

A further aspect of the present invention is directed to a method of screening compounds for protein interaction. This method involves providing a protein array according to the present invention, contacting the array with compounds to be screened, and detecting compounds that interact with the first and/or second protein, thereby screening compounds for protein interaction.

A wide range of detection methods is applicable to this method of the present invention. As desired, detection may be either quantitative or qualitative. Thus, the array of the present invention can be interfaced with optical detection methods such as absorption in the visible or infrared range, chemoluminescence, and fluorescence (including lifetime, polarization, fluorescence correlation spectroscopy (FCS), and fluorescence-resonance energy transfer (FRET)), which are well-known in the art. Furthermore, other modes of detection such as those based on optical waveguides (PCT Publication No. WO 96/26432 and U.S. Pat. No. 5,677,196, which are hereby incorporated by reference in their entirety), surface plasmon resonance, surface charge sensors, and surface force sensors are compatible with many embodiments of the present invention.

Although non-label detection methods are generally preferred, some of the types of detection methods commonly used for traditional immunoassays which require the use of labels may be applied to use with at least some embodiments of the array of the present invention, especially those arrays which are arrays of protein-capture agents. These techniques include noncompetitive immunoassays, competitive immunoassays, and dual label, ratiometric immunoassays. These particular techniques are primarily suitable for use with the arrays of proteins when the number of different proteins with different specificity is small (less than about 100). In the competitive method, binding-site occupancy is determined indirectly. In this method, the proteins of the array are exposed to a labeled developing agent, which is typically a labeled version of the analyte or an analyte analog. The developing agent competes for the binding sites on the protein with the analyte. The fractional occupancy of the proteins on different patches can be determined by the binding of the developing agent to the proteins of the individual spots. In the noncompetitive method, binding site occupancy is determined directly. In this method, the spots of the array are exposed to a labeled developing agent capable of binding to either the bound analyte or the occupied binding sites on the protein. For instance, the developing agent may be a labeled antibody directed against occupied sites (i.e., a "sandwich assay"). Alternatively, a dual label, ratiometric, approach may be taken where the immobilized protein is labeled with one label and the second, developing agent is labeled with a second label (Ekins et al., *Clinica Chimica Acta* 194:91-114 (1990), which is hereby incorporated by reference in its entirety). Many different labeling methods may be used in the aforementioned techniques, including radioisotopic, enzymatic, chemiluminescent, and fluorescent methods.

The screening method of the present invention may be carried out for screening a plurality of proteins for their ability to bind a particular component of a sample. This method comprises delivering the sample to a protein array of the present invention comprising the proteins to be screened and detecting, either directly or indirectly, the presence or amount of the particular component retained at each spot. In one embodiment, the method further comprises the intermediate step of washing the array to remove any unbound or nonspecifically bound components of the sample from the array before the detection step. In another embodiment, the method further comprises the additional step of further characterizing the particular component retained on at least one spot. The particular component may optionally be a protein.

In another embodiment of the invention, a method of assaying for protein-protein binding interactions is provided which comprises the following steps: first, delivering a sample comprising at least one protein to be assayed for binding to the protein array of the invention; and then detecting, either directly, or indirectly, for the presence or amount of the protein from the sample which is retained at each spot. In a preferred embodiment, the method further comprises an additional step prior to the detection step which comprises washing the array to remove unbound or nonspecifically bound components of the sample from the array. The protein being assayed for binding may be from the same organism as the proteins immobilized on the array.

Another embodiment of the invention provides a method of assaying in parallel for the presence of a plurality of analytes in a sample which can react with one or more of the immobilized proteins on the protein array of the present invention. This method involves delivering the sample to the array and detecting for the interaction of the analyte with the immobilized protein at each spot on the array.

In still another embodiment of the invention, a method of assaying in parallel for the presence of a plurality of analytes in a sample which can bind one or more of the immobilized proteins on the protein array involves delivering the fluid sample to the invention array and detecting, either directly or indirectly, the presence or amount of analyte retained at each spot. In a preferred embodiment, the method further comprises the step of washing the array to remove any unbound or non-specifically bound components of the sample from the array.

The array of the present invention may be used in a diagnostic manner when the plurality of analytes being assayed are indicative of a disease condition or the presence of a pathogen in an organism. In such embodiments, the sample which is delivered to the array will then typically be derived from a body fluid or a cellular extract from the organism.

The array may be used for drug screening when a potential drug candidate is screened directly for its ability to bind or otherwise interact with a protein or plurality of proteins on the array of the present invention. Alternatively, a plurality of potential drug candidates may be screened in parallel for their ability to bind or otherwise interact with one or more immobilized proteins on the array. The drug screening process may optionally involve assaying for the interaction, such as binding, of at least one analyte or component of a sample with one or more immobilized proteins on an array of the present invention, both in the presence and absence of the potential drug candidate. This allows for the potential drug candidate to be tested for its ability to act as an inhibitor of the interaction or interactions originally being assayed.

EXAMPLES

The following examples are provided to illustrate embodiments of the present invention but are by no means intended to limit its scope.

Example 1

Print: Both PBS Buffers and Sodium Borate Buffer

This protocol is for the application of orienting GST-fusion proteins (lectins) on an activated NHS-surface in situ by printing in an optimized buffer containing glutathione (GSH). To begin, optimal buffer conditions and optimal GSH concentrations were needed for the printing process. Noting that pH would affect the printing and GSH coupling process, three different buffers were chosen for experimental prints: 10 mM sodium phosphate buffer (PBS, pH 7.2), 10 mM sodium phosphate buffer (pH 7.8), and 50 mM sodium borate buffer (pH 8.5).

For the preliminary work, this small set of buffers was supplemented with 250 mM, 50 mM, 10 mM, and 1 mM GSH (Thermo Fisher Scientific, Rockford, Ill.), and GafD was used as a model lectin (printed at 20, 10, and 5 µM). For a control, a standard printing buffer (PBS, pH 7.6) was used.

Each lectin solution was printed with 0.5 mg/mL bovine serum albumin (BSA, fraction V, Fisher), 1 mM $CaCl_2$, 1 mM $MgCl_2$, and 1 mM N-acetylglucosamine (GlcNAc, Fisher). The solutions were loaded into 384-well microtiter plates (Whatman, Piscataway, N.J.) and placed into the SpotBot 2 Personal Microarrayer (ArrayIt Corp., Sunnyvale, Calif.) using SMP3 pins (ArrayIt), which fabricate spots ~100 µm in area. The printing chamber was kept at a constant humidity around 50% and the source plate was kept at 8° C. Prior to the print, a print file was generated using the MMF Spocle program. After the print was finished, the cold plate was turned off and the slides were incubated and warmed to room temperature over 2 hrs. After 2 hrs, the slides were placed into a coplin jar containing slide blocking buffer (50 mM ethanolamine in 100 mM sodium borate buffer, pH 8.5) and incubated at room temperature for 1 hr. Slides were then washed with PBS containing 0.05% Tween®-20 (0.05% PBS-T, 3×3 min) and then washed once with PBS. Slides were dried with a slide spinner (Labnet Intl., Edison, N.J.), and then affixed to a 24-well microarray gasket (ArrayIt). Slides were then hybridized with Cy5-labeled chicken egg ovalbumin ("OVA-Cy5") in PBS containing 0.005% Tween®-20 (0.005% PBS-T, 1 mM $CaCl_2$, and 1 mM $MgCl_2$ (100 µL per well, at concentrations of 0.4 µM of OVA-Cy5)) and incubated at room temperature for 2 hrs. After incubation, the wells were aspirated and washed with PBS containing 0.005% Tween® (0.005% PBS-T, 3×3 min). The gaskets were then removed and the slides were placed into a coplin jar filled with PBS and washed for 3 min, then dried using the slide spinner and scanned using a Genepix 4100A slide scanner (Molecular Devices Corp., Union City, Calif.). Genepix Pro 5.1 software was used to extract data and Microsoft Excel software was used for statistical analysis and for generating tables and graphs.

Example 2

Print: Sodium Borate Buffer and Sodium Bicarbonate

In the experiment described in Example 1, it was found that lectins could be oriented in situ. Another experiment was to test whether sodium bicarbonate buffer could be used. Accordingly, GafD (20 µM) and RS-IIL (11.5 µM) were prepared in 50 mM sodium borate buffer (pH 8.5) and 100 mM sodium bicarbonate buffer (pH 9.3). Each solution was supplemented with 0.5 mg/mL BSA (fraction V, Fisher), 1 mM $CaCl_2$, 1 mM $MgCl_2$, and either 1 mM GlcNAc (GafD) or 1 mM mannose (RS-IIL). The lectin solutions were also supplemented with 100, 50, 25, and 10 mM GSH. The solutions were loaded into 384-well microtiter plates (Whatman, Piscataway, N.J.) and placed into the SpotBot 2 Personal Microarrayer (ArrayIt Corp., Sunnyvale, Calif.) using SMP3 pins (ArrayIt), which fabricate spots ~100 µm in area. The printing chamber was kept at a constant humidity around 50% and the source plate was kept at 8° C. Prior to the print, a print file was generated using the MMF Spocle program. After the print was finished, the cold plate was turned off and the slides were incubated and warmed to room temperature over 2 hrs. After 2 hrs, the slides were placed into a coplin jar containing slide blocking buffer (50 mM ethanolamine in 100 mM sodium borate buffer, pH 8.5) and incubated at room temperature for 1 hr. Slides were then washed with PBS containing 0.05% Tween®-20 (0.05% PBS-T, 3×3 min) and then washed once with PBS. Slides were dried with a slide spinner (Labnet Intl., Edison, N.J.), and then affixed to a 24-well microarray gasket (ArrayIt). Slides were then hybridized with Cy5-labeled chicken egg ovalbumin (OVA-Cy5, 5 µM, 100 µL total volume), and Cy3-labeled RNase B (RNase B-Cy3, 2.5 µM, 100 µL total volume) in 0.005% PBS-T, 1 mM $CaCl_2$, and 1 mM $MgCl_2$ and incubated at room temperature for 2 hrs. After incubation, the wells were aspirated and washed with 0.005% PBS-T (3×3 min). The gaskets were then removed and the slides were placed into a coplin jar filled with PBS and washed for 3 min, then dried using the slide spinner and scanned using a Genepix 4100A slide scanner (Molecular Devices Corp., Union City, Calif.). Genepix Pro 5.1 software was used to extract data and Microsoft Excel software was used for statistical analysis and for generating tables and graphs.

Example 3

Print: Sodium Borate (100 mM and 50 mM GSH) with Plant Lectins

With the experiment in Example 2, it was found that the sodium borate buffer gave the best signals. It was still unclear whether 100 or 50 mM GSH is the better buffer supplement. It was decided to print GafD (20, 10, 5, 2.5, and 1.25 µM) and RS-IIL (23, 11.5, 5.8, 2.9, 1.4 µM) along with DSA (6 µM), ConA (10 µM), and WGA (28 µM). The recombinant lectins (GafD and RS-IIL) were prepared in 50 mM sodium borate buffer (pH 8.5) supplemented with 100 and 50 mM GSH, while the plant lectins (DSA, ConA, and WGA) were diluted in PBS. Each solution was supplemented with 0.5 mg/mL BSA (fraction V, Fisher), 1 mM $CaCl_2$, 1 mM $MgCl_2$, and either 1 mM GlcNAc (GafD, DSA, and WGA) or 1 mM mannose (RS-IIL and ConA). The solutions were loaded into 384-well microtiter plates (Whatman, Piscataway, N.J.) and placed into the SpotBot 2 Personal Microarrayer (ArrayIt Corp., Sunnyvale, Calif.) using SMP3 pins (ArrayIt), which fabricate spots ~100 µm in area. The printing chamber was kept at a constant humidity around 50% and the source plate was kept at 8° C. Prior to the print, a print file was generated using the MMF Spocle program. After the print was finished, the cold plate was turned off and the slides were incubated and warmed to room temperature over 2 hrs. After 2 hrs, the slides were placed into a coplin jar containing slide blocking buffer (50 mM ethanolamine in 100 mM sodium borate buffer, pH 8.5) and incubated at room temperature for 1 hr. Slides were then washed with PBS containing 0.05% Tween®-20 (0.05% PBS-T, 3×3 min) and then washed once with PBS. Slides were dried with a slide spinner (Labnet Intl., Edison, N.J.), and then affixed to a 24-well microarray gasket (ArrayIt). Slides were then hybridized with Cy5-labeled chicken egg ovalbumin (OVA-Cy5, 10 µM, 100 µL total volume) and Cy5-labeled cell membrane extracts of Sk-Mel-5 (Sk-Me1-5-Cy5, 1.5 µg, 100 µL total volume) in 0.005% PBS-T, 1 mM $CaCl_2$, and 1 mM $MgCl_2$ and incubated at room temperature for 2 hrs. After incubation, the wells were aspirated and washed with 0.005% PBS-T (3×3 min). The gaskets were then removed and the slides were placed into a coplin jar filled with PBS and washed for 3 min, then dried using the slide spinner and scanned using a Genepix 4100A slide scanner (Molecular Devices Corp., Union City, Calif.). Genepix Pro 5.1 software was used to extract data and Microsoft Excel software was used for statistical analysis and for generating tables and graphs. Error bars represent the standard deviation from the median values. For inhibition experiments, selected arrays were incubated with 200 mM monosaccharide (50 µL total volume), and arrays not inhibited were incubated with 0.005% PBS-T (50 µL). Arrays were incubated for 30 min, and then appropriate amounts of sample were added to make 100 µL total volume per array.

Example 4

Print: GST-GafD, tc-GafD Comparisons

To demonstrate that lectins are being oriented in situ via the specific GST-GSH interaction, GafD preps from prior work were printed. Specifically, Cy5-labeled GST-GafD (GST-GafD), Cy5-labeled thrombin-cleaved GafD (tc-GafD-Cy5), and unlabeled, thrombin-cleaved GafD (tc-GafD) were printed. It was decided to print all three GafD preps and GST-GafD (10, 5, 2.5, 1.25, and 0.63 µM) and they were prepared in 50 mM sodium borate buffer (pH 8.5) supplemented with 100 mM GSH. Each solution was supplemented with 0.5 mg/mL BSA (fraction V, Fisher), 1 mM $CaCl_2$, 1 mM $MgCl_2$, and 1 mM GlcNAc. The solutions were loaded into 384-well microtiter plates (Whatman, Piscataway, N.J.) and placed into the SpotBot 2 Personal Microarrayer (ArrayIt Corp., Sunnyvale, Calif.) using SMP3 pins (ArrayIt), which fabricate spots ~100 µm in area. The printing chamber was kept at a constant humidity around 50% and the source plate was kept at 8° C. Prior to the print, a print file was generated using the MMF Spocle program. After the print was finished, the cold plate was turned off and the slides were incubated and warmed to room temperature over 2 hrs. After 2 hrs, the slides were placed into a coplin jar containing slide blocking buffer (50 mM ethanolamine in 100 mM sodium borate buffer, pH 8.5) and incubated at room temperature for 1 hr. Slides were then washed with PBS containing 0.05% Tween®-20 (0.05% PBS-T, 3×3 min) and then washed once with PBS. Slides were dried with a slide spinner (Labnet Intl., Edison, N.J.), and then affixed to a 24-well microarray gasket (ArrayIt). Slides were then hybridized with α-S·tag antibody conjugated with phycoerythrin (α-S·tag-PE, 1 µg/mL, 100 µL total volume) in 0.005% PBS-T, 1 mM CaCl$_2$, and 1 mM MgCl$_2$, and 1% BSA and incubated at room temperature for 2 hrs. After incubation, the wells were aspirated and washed with 0.005% PBS-T (3×3 min). The gaskets were then removed and the slides were placed into a coplin jar filled with PBS and washed for 3 min, then dried using the slide spinner and scanned using a Genepix 4100A slide scanner (Molecular Devices Corp., Union City, Calif.). Genepix Pro 5.1 software was used to extract data and Microsoft Excel software was used for statistical analysis and for generating tables and graphs.

Figure 2:
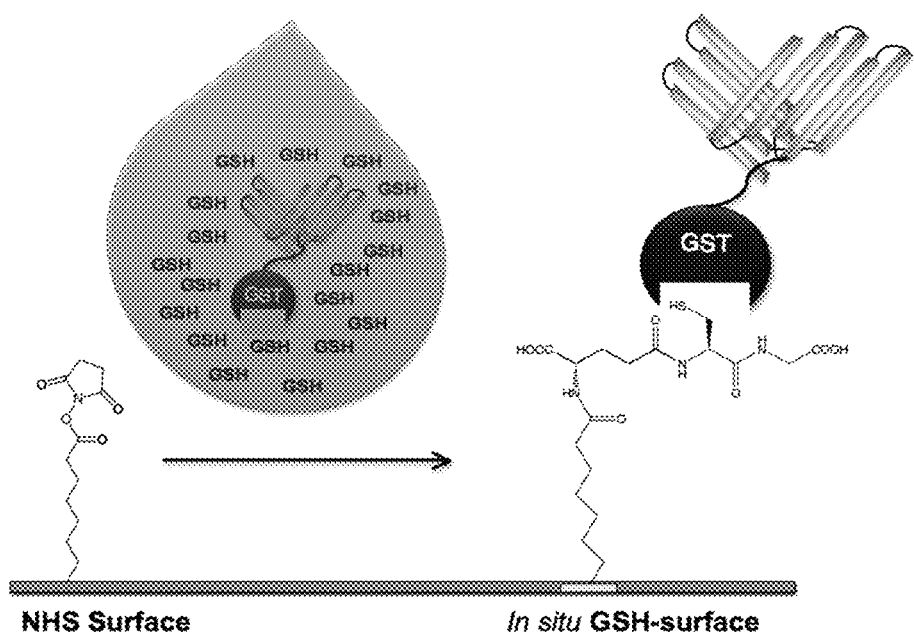
FIG. 2 is a schematic illustration showing in situ orientation of GST-proteins via competitive GSH-modification of a slide surface.
Figure 3:
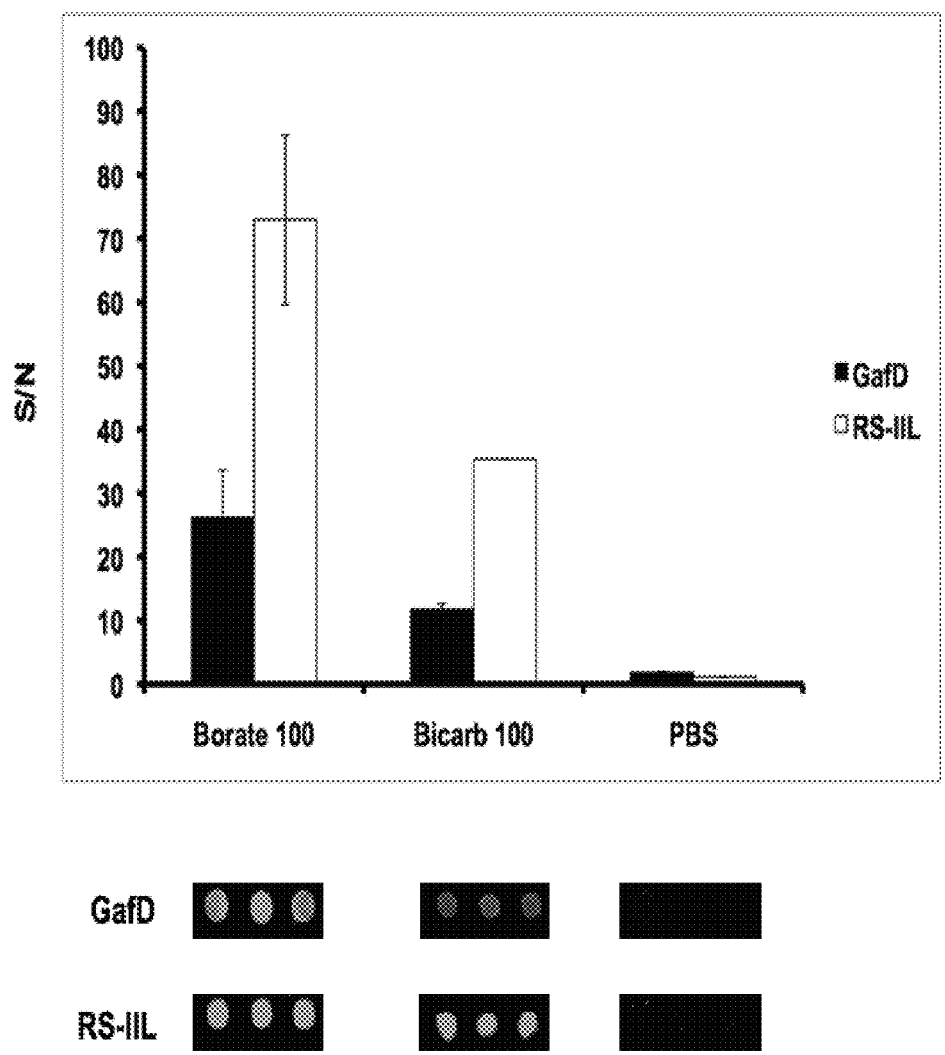
FIG. 3 is a graphical illustration showing that borate buffer supplemented with 100 mM GSH is, according to one embodiment, an optimal print buffer for oriented lectin microarrays. GST-GafD or GST-RS-IIL were printed at identical concentrations in one of three buffers: Borate 100 (50 mM sodium borate buffer (pH 8.5), 100 mM GSH); Bicarb 100 (100 mM NaHCO$_3$, 100 mM GSH); and PBS (pH 7.6). All print buffers were supplemented with 0.5 mg/mL bovine serum albumin ("BSA"), 1 mM CaCl$_2$, 1 mM MgCl$_2$, and 1 mM N-acetylglucosamine ("GlcNAc"). The array was probed with RNase B-Cy3 (2.5 μM) and the signal to noise ratio (S/N) was used as a measurement of relative activity. Graphical representation of activity of RNase B-Cy3 (2.5 μM) against GafD (20 μM, closed bars) and RS-IIL (11.5 μM, open bars) in different glutathione (GSH) buffers is shown. Error bars represent the standard deviation from the median values.

The present invention provides a means by which recombinant GST-proteins (including lectins), can be printed with orientation on the same arrays as naturally derived proteins. This enables one to take advantage of orientation (i.e., better protein activity) without loss of the diversity on a microarray. The initial idea was to take advantage of the small molecule nature of glutathione and/or more nucleophilic derivatives, if needed, to see whether NHS-slides (Nexterion® Slide H, SCHOTT North America, Inc., Elmsford, N.Y.) could be modified with glutathione in the presence of the GST-modified protein, allowing creation of a GSH-surface in situ to which the protein would presumably bind. A general scheme is illustrated in FIG. 2. It was reasoned that the coupling of the protein, via surface lysines, might be kinetically less favored due to restriction of the orientations available to it, than the small molecule glutathione. To this end, it was tested whether the simple addition of glutathione to the print buffer of proteins would engender protein orientation on an NHS-activated slide, and thus higher levels of protein activity. In earlier work, various buffers were tested for the modification of NHS-slides with glutathione, prior to the printing of the lectin, and it was found that higher pH buffers were optimal. Due to concerns about lectin activity at high pH, small panel of buffers were tested in initial experiments. Of the three buffers tested, borate buffer (pH=8.5) supplemented with 50 mM or more glutathione (and standard print buffer additives (Hsu et al., "A Simple Strategy for the Creation of a Recombinant Lectin Microarray," *Mol. Biosyst.* 4(6):654-62) (2008), which is hereby incorporated by reference in its entirety) worked well for in situ orientation as assessed by lectin activity (FIG. 3).

100 mM GSH in borate buffer was used in future experiments. Printing with this buffer gave lectins that were ~25-70-fold more active than the same lectin printed in the standard print buffer (PBS pH=7.6, + standard additives). Previous work has shown that on a GSH-surface, smaller amounts of protein bind but the protein is more highly active, leading to the belief that the enhancement in observed activity is due to orientation.

Figure 4:
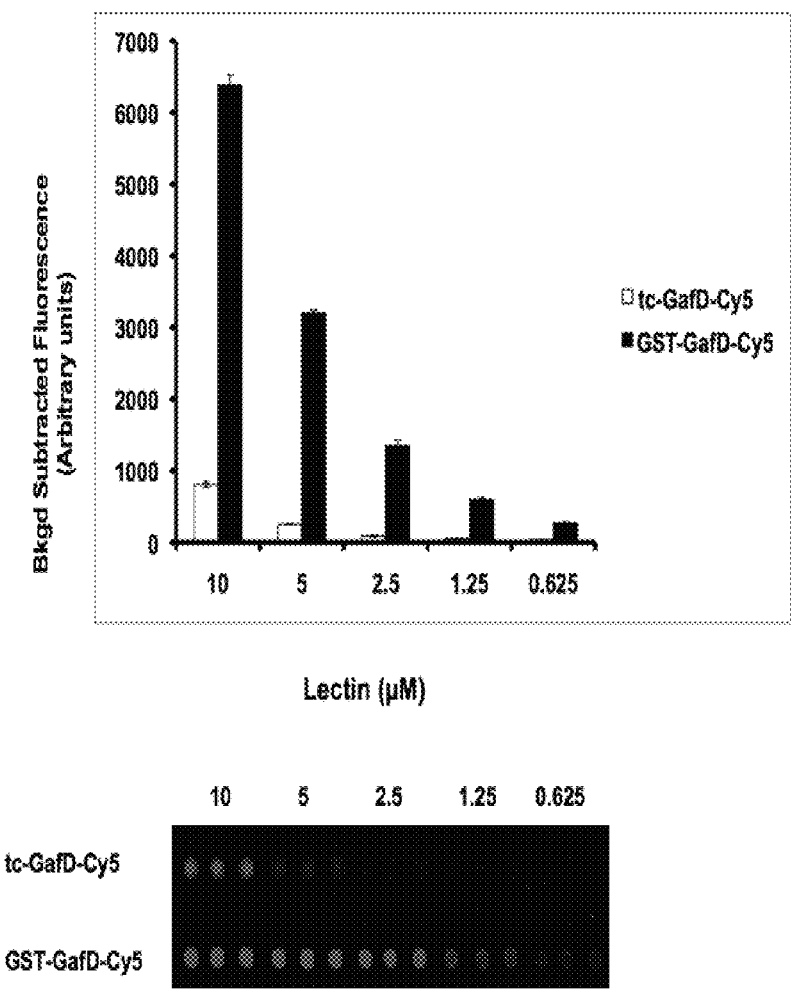
FIG. 4 is a graphical representation of Cy5-labeled GST-GafD (GST-GafD-Cy5, closed bars) and thrombin-cleaved GafD-Cy5 (tc-GafD-Cy5, open bars) printed in sodium borate buffer with 100 mM GSH. Background subtracted fluorescence was used for deposition analysis. Error bars represent the standard deviation from the median values.
Figure 5:
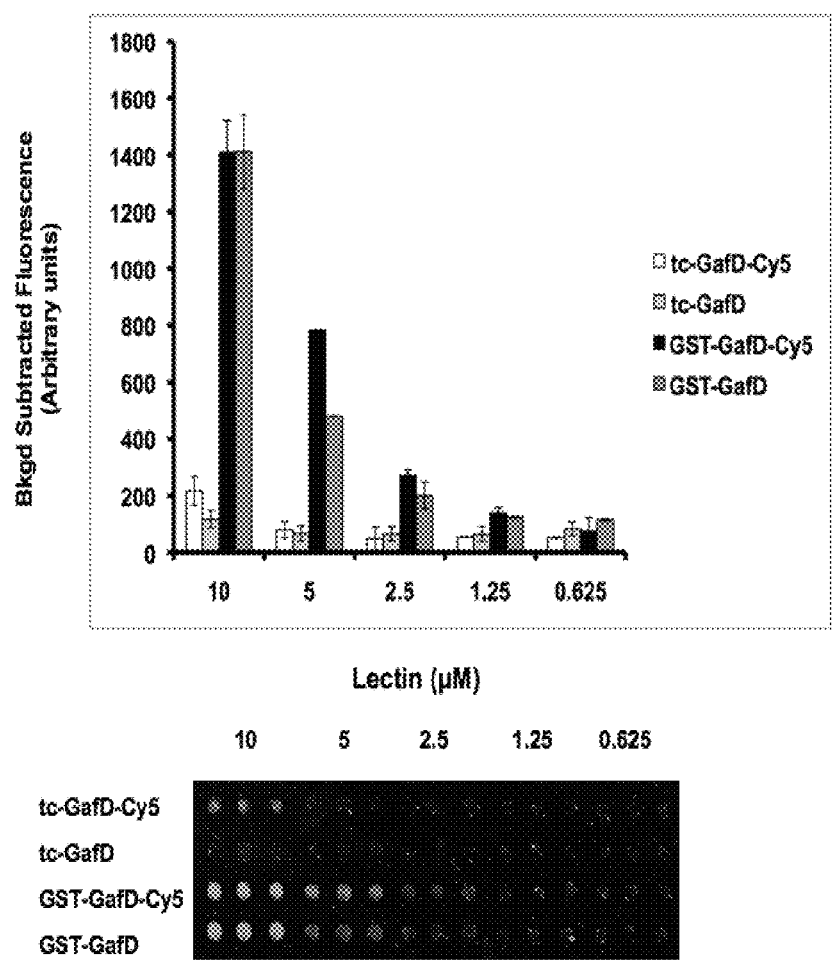
FIG. 5 is a graphical representation of indirect detection of GafD preparations using an α-S·tag antibody derivatized with phycoerythrin (α-S·tag-PE). Cy5-labeled GST-GafD (GST-GafD-Cy5, closed bars), GST-GafD (GST-GafD, dark-shaded bars), thrombin cleaved GafD (tc-GafD, light-shaded bars) and thrombin-cleaved GafD-Cy5 (tc-GafD-Cy5, open bars) printed in sodium borate buffer with 100 mM GSH. Background subtracted fluorescence was used for deposition analysis.

As previously observed for non-oriented lectins, lectin activity could be inhibited using monosaccharides, proving that the signal observed is due to lectin activity and not non-specific binding of the Cy3-labeled glycoprotein. To assess whether a GST-GSH interaction is responsible for the observed enhanced activity, the deposition was tested, under these conditions, of Cy5-labeled GST-GafD and Cy5-thrombin-cleaved (tc)-GafD, which no longer has the GST motif. As shown in FIG. 4, significantly less deposition of the Cy5-tc-GafD was observed (~7-fold at 10 µM lectin). To confirm that this is due to protein deposition and not just uneven labeling of the two proteins, the microarrays, which also contained unlabelled lectin, were incubated with a phycoerythrin-labeled anti-S-tag antibody, which can detect a tag common to all four versions of the protein (Cy5-labeled and unlabelled, GST-GafD and tc-GafD). As shown in FIG. 5, only low amounts of the tc-GafD were observed on the in situ GSH-treated surfaces. Taken together, these data confirm that a GST-GSH interaction is responsible for binding of the GST-modified protein under these conditions. Thus, the GSH successfully outcompetes the protein for the surface, allowing it to coat the surface prior to the protein settling down and enabling in situ orientation.

Example 5

Pentameric Antibody IgM and Dimeric Antibody IgA

The inventors herein demonstrate a general strategy to orient proteins on an in situ modified solid support. This work was adapted to perform a one-pot orientation of untagged IgG antibodies via, e.g., GST-fusion proteins of Protein A (SpA) and Protein G (SpG), which bind to the Fc domains of antibodies. IgG antibodies are monomeric, but two other antibodies—IgM and IgA—are pentameric and dimeric in nature, as shown in FIG. 6. These multimeric antibodies are bound together via the Fc domains, thus complicating the orientation strategy of the GST-SpA and -SpG proteins. Aside from these well-characterized SpA and SpG antibody-binding proteins, another protein from *Peptostreptococcus magnus*, PpL, was found to bind to the light-chain fragments of antibodies with kappa (κ) light chains (Graille et al., "Complex Between *Peptostreptococcus magnus* Protein L and a Human Antibody Reveals Structural Convergence in the Interaction Modes of Fab Binding Proteins," *Structure* 9(8):679-87 (2001); Housden et al., "Immunoglobulin-Binding Domains: Protein L From *Peptostreptococcus magnus*," *Biochem. Soc. Trans.* 31:716-18 (2003); Muzard et al., "Grafting of Protein L-Binding Activity Onto Recombinant Antibody Fragments," *Anal. Biochem.* 388(2):331-38 (2009), which are hereby incorporated by reference in their entirety). In mammals, only lambda (λ) and κ light chains are present on antibodies, and of the mammals, only mouse, rat, rabbit, and humans are known to contain protein L-binding κ chains (Nilson et al., "Purification of Antibodies Using Protein L-Binding Framework Structures in the Light Chain Variable Domain," *J. Immun. Meth.* 164(1):33-40 (1993), which is hereby incorporated by reference in its entirety). Ideally, a GST-PpL fusion protein would bind to a κ chain fragment from a multivalent antibody, and become oriented upon printing in the GSH-containing buffer described herein.

Example 6

Fc Binding Domains of SpA and SpG

Figure 7:
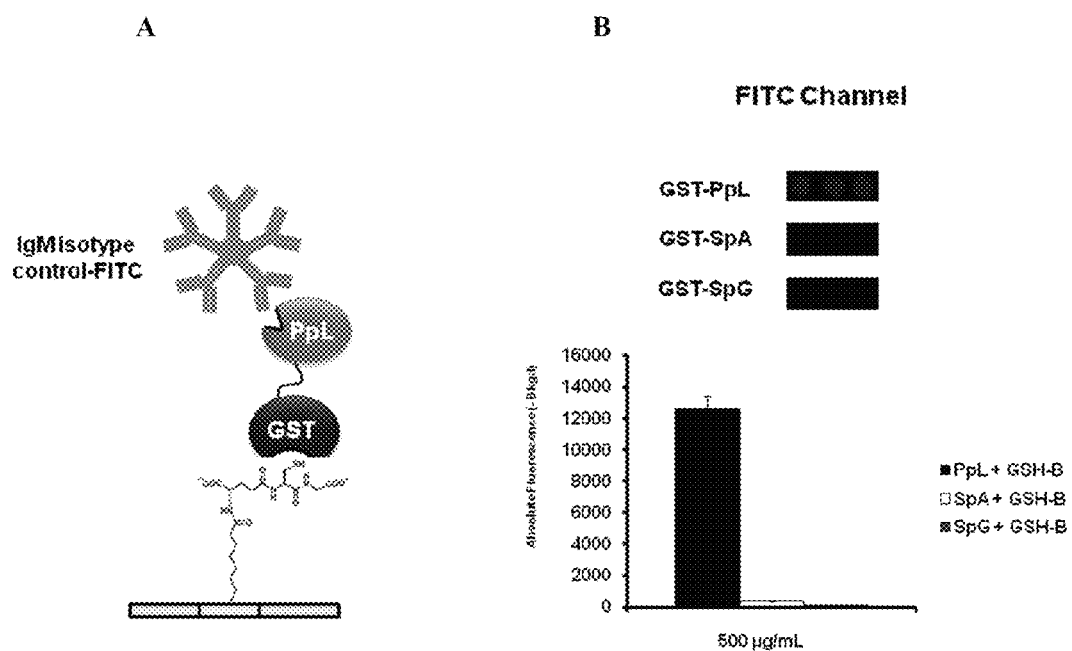
FIGS. 7A-B show GST-Protein L (GST-PpL), GST-Protein A (GST-SpA), and GST-Protein G (GST-SpG) printed in GSH-B and tested for binding activity against a FITC-conjugated IgM isotype control (IgM-FITC).

To show that the Fc binding domains of SpA and SpG would not suffice with a multivalent antibody system, GST-SpA, -SpG, and -PpL were printed in a prepared in situ orientation buffer (GSH-B, 100 mM GSH in 50 mM sodium borate, pH 8.5), and the deposited array was probed with a FITC-labeled IgM isotype control, as shown in FIGS. 7A-B. No significant binding of the Fc-binding proteins to the FITC-labeled isotype control (IgM-FITC) was observed. However, binding between the Protein L GST-fusion protein was observed, thus proving that, conceptually, the antibody can be captured via, presumably, the κ light chain binding interaction. From this set of data, it was determined that GST-PpL may be a suitable protein to capture IgM antibodies, and that the effectiveness in κ light chain binding is enhanced upon orientation via the GST-GSH interaction previously described.

Example 7

IgM One-Pot Methodology

Figure 8:
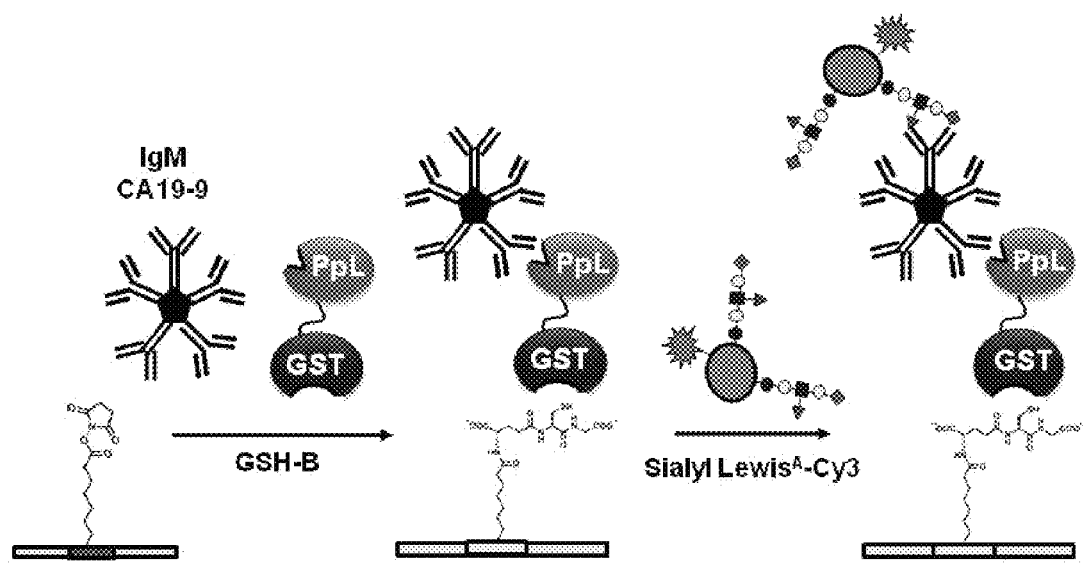
FIG. 8 is a schematic illustration of the in situ orientation of the Sialyl Lewis$^a$-specific IgM antibody (CA19-9) by GST-PpL in GSH-B. When the three-component mixture is deposited onto the NHS-activated surface, the GSH reacts first, forming a micro-layer of GSH, upon which the GST-PpL is immobilized, orienting the Protein L. The Protein L domain then binds to the κ chains of CA19-9, thus orienting the antibody and presenting the carbohydrate recognition domains in a more favorable manner.
Figure 9:
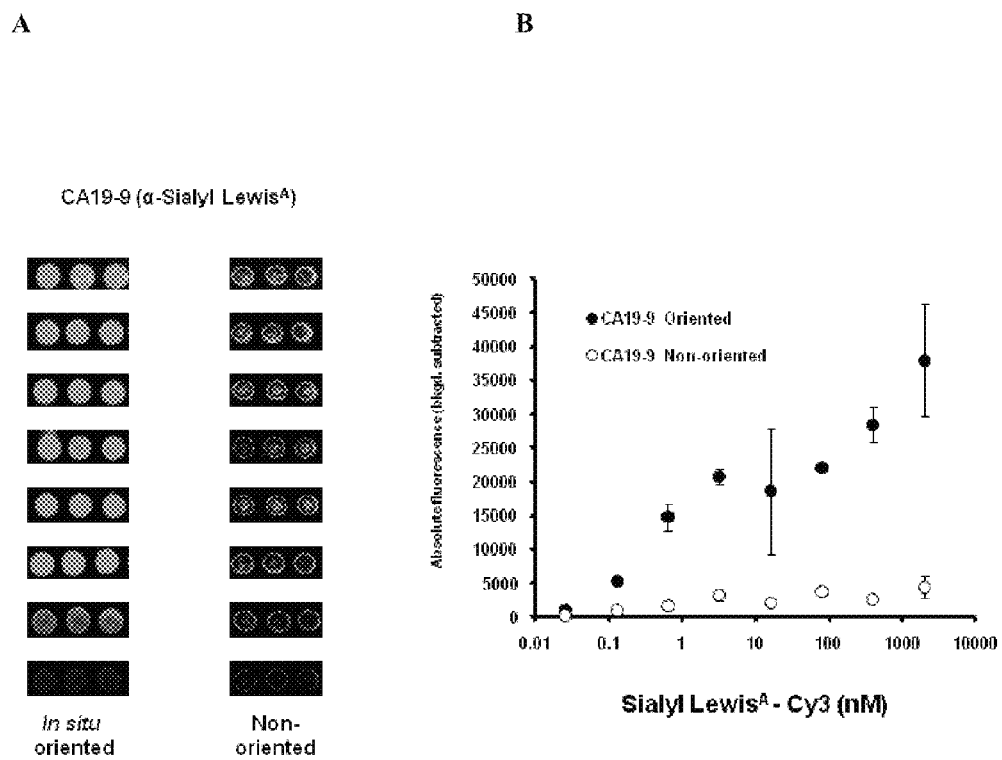
FIGS. 9A-B show the effects of in situ orientation on the activity of CA19-9.

Once it was established that Protein L can be used to tether IgM antibodies, the next step was to condense the orientation of IgM into a one-pot methodology. To test this technique, CA19-9 was printed with GST-PpL in GSH-B and the activity of the immobilized CA19-9 was probed with Sialyl Lewis$^{\alpha}$-Cy3, as illustrated by FIG. 8. As shown in FIG. 9A, when printed all together, the activity of the displayed CA19-9 antibody is much higher than randomly deposited, or non-oriented, antibody in the standard print buffer (PB: 10 mM sodium phosphate, 15 mM sodium chloride, 0.5 mg/mL BSA, CA19-9+PB). As shown in FIG. 9B, the activity of oriented CA19-9 was significantly higher than non-oriented antibody. When arrays were treated with varying amounts of Sialyl Lewis$^{\alpha}$-Cy3, a general increase in activity was observed, when comparing the oriented CA19-9 to the non-oriented CA19-9.

Figure 10:
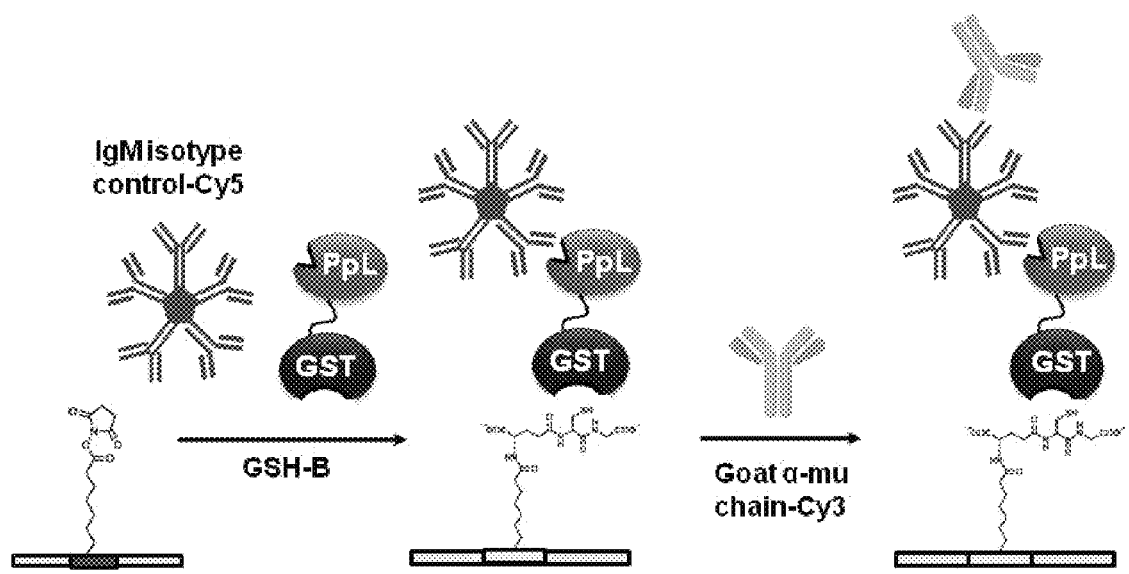
FIG. 10 is a schematic illustration of the in situ orientation of a Cy5-labeled IgM isotype control (IgM-Cy5) by GST-PpL in GSH-B. When the three-component mixture is deposited onto the NHS-activated surface, the GSH reacts first, forming a micro-layer of GSH, upon which the GST-PpL is immobilized, orienting the Protein L. The Protein L domain then binds to the κ chains of IgM-Cy5, thus orienting the antibody and presenting the μ heavy chains in a more favorable manner to be detected by a Cy3-conjugated goat α-mu chain antibody (goat α-mu-Cy3).
Figure 11:
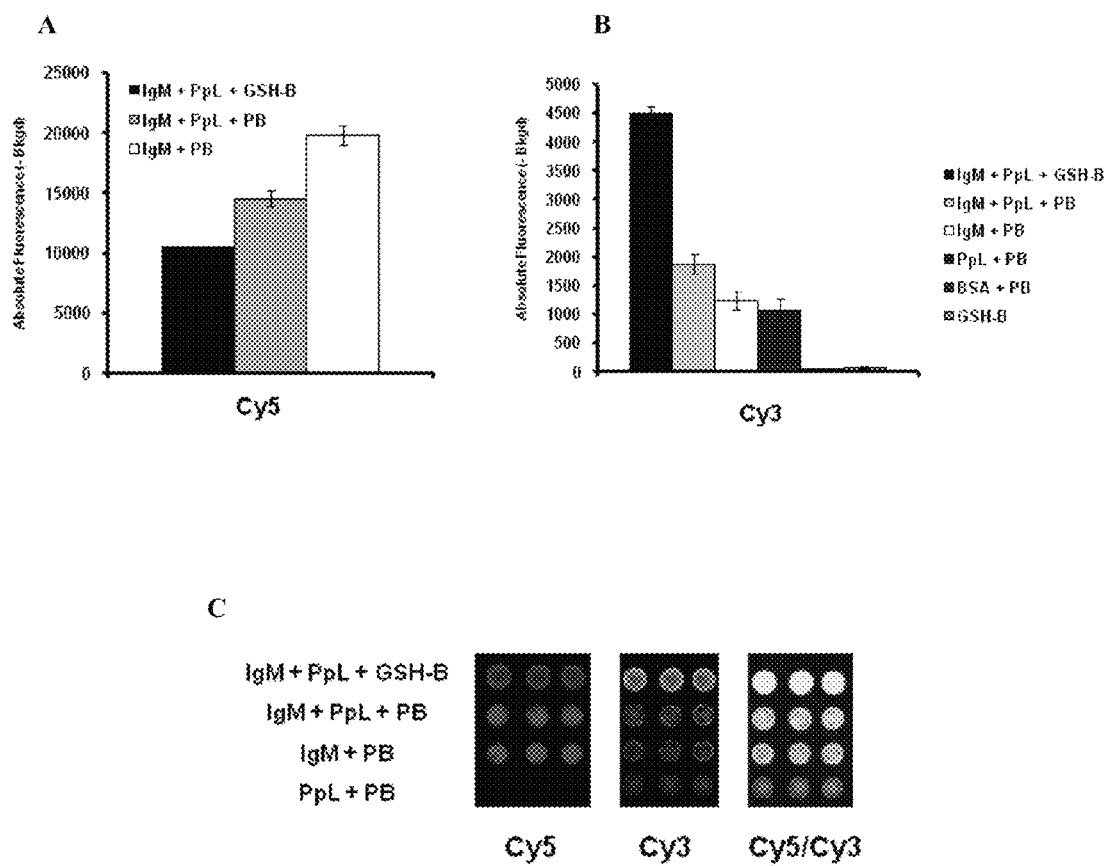
FIGS. 11A-C show in situ orientation of IgM-Cy5 and detection by goat α-mu chain-Cy3.

In order to determine if the in situ orientation method results in a greater amount of protein deposition, instead of an oriented antibody, a dual-color experiment was performed. An IgM isotype control was labeled with Cy5-NHS and printed (0.3 mg/mL) with GST-PpL (0.02 mg/mL) in GSH-B. The array was then probed with goat α-mu (p) chain antibody conjugated to DyLight 549 (1 µg/mL) and scanned in both Cy5 and Cy3 channels, as illustrated by FIG. 10. For comparison, the same Cy5-labeled IgM antibody was printed in PB. Deposited antibody was observed through the Cy5 channel in which there was a 2-fold increase of antibody deposited under the standard print conditions (FIGS. 11A, C). However, when detecting the accessibility of the deposited antibody in the Cy3 channel, more than 2.5-fold increase of the presentation of the µ chain of the deposited IgM antibody was observed (FIGS. 11B, C), indicating a better displayed, or oriented, antibody.

Example 8

Print: GST-PpL Fusion Protein

Figure 12:
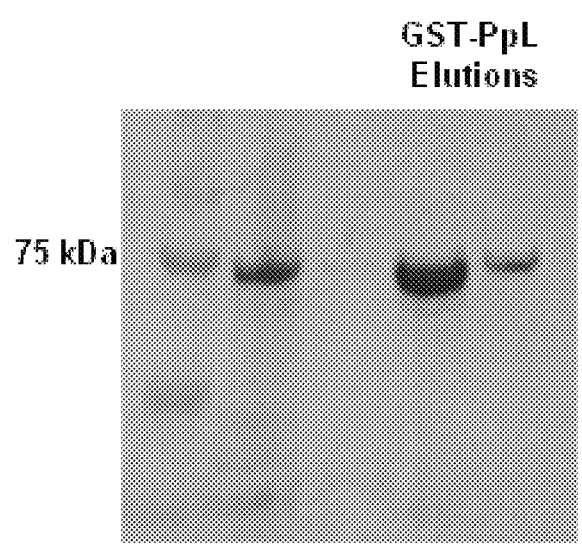
FIG. 12 illustrates the result of purification of GST-PpL monitored by 10% SDS-PAGE gel. The newly created GST-PpL protein is ~75 kDa in size.

IgM antibody isotype control (Abcam, ab18400) was labeled with Cy5-NHS (GE Healthcare, PA15104) and 100 mM sodium bicarbonate (pH 9.3) for 1 hour. The sample was then dialyzed against PBS (10 mM sodium phosphate, 15 mM sodium chloride) and stored at 4° C. until future use (IgM-Cy5). The protein L gene from *Peptostreptococcus magnus* was synthesized by Genewiz (Piscataway, N.J.). PpL was cloned out of the synthesized genes with the following primers: Forward: 5' GAC GAC GAC AAG ATG AAA GAG GAA ACC CCG (SEQ ID NO: 1) 3' and Reverse: 5' GAG GAG AAG CCC GGT TTA ACC GGC GAA ACG AAT G (SEQ ID NO: 2) 3'. PCR reactions were performed with the Hot Start DNA Polymerase (New England Biolabs, #F120S) and reactions were tailored to product specifications. PCR products were treated and ligated into the pET-41 Ek/LIC kit (Novagen, #71017-3) according to the manufacturer's directions. cDNA was then transformed into electrocompetent NovaBlue Gigasingles (Novagen, #71227), grown, and purified DNA was obtained using the Qiaprep Mini Kit (Qiagen, #27106), and sequenced. Positive sequences were transformed into electrocompetent BL21 (DE3) cells, and grown on LB-Agar supplemented with kanamycin (30 µg/mL). Colonies were picked for overnight growth in LB, and were then inoculated into 1 L of LB supplemented with kanamycin (30 µg/mL). Cultures were grown to an OD$_{600}$ 0.7-1.0, then induced with 0.2 mM IPTG and grown for 3 hrs at 37° C., shaking at 250 rpm. Cells were pelleted (3000×g, 15 min) and resuspended in 40 mL of lysis buffer (PBS+0.2% Triton-X10) with protease inhibitor mix. Lysozyme (~1 mg/mL) was added and mixed on ice for 30 minutes. DNase I (New England Biolabs #M0303, ~5 units/ mL of lysate) was added and mixed for 10 minutes on ice. The mixture was then centrifuged at 30,000×g for 30 minutes. The supernatant was loaded onto a 1 mL GSH-sepharose column (GE Healthcare, #17-0756-01), washed with 10 mL of PBS, eluted with 10 mM GSH in 50 mM Tris, pH 8.0, and collected in 1 mL fractions. Purification was analyzed by SDS-PAGE, as illustrated by FIG. 12, and fractions containing sample were pooled and dialyzed against PBS. Aliquots were prepared and snap frozen in liquid N$_2$ and stored at −80° C. until needed. Protein L, which is a gene synthesized by Genewiz (bolded sequence (SEQ ID NO: 3) is the gene fragment cloned into the pET-41 vector), is shown below as SEQ ID NO: 4:

ATGAAAAAAACGGCGATTGCTATTGCTGTGGCTCTGGCAGGATTTGCT

ACTGTTGCTCAAGCGGCTGTCGAAAACAAAGAGGAAACCCCGGAAACA

CCTGAAACCGATTCGGAAGAAGAAGTGACGATCAAAGCGAACCTGATT

TTTGCCAATGGCAGCACCCAAACAGCGGAATTCAAAGGCACCTTCGAG

AAAGCGACCTCTGAAGCATATGCCTATGCCGATACGCTGAAAAAAGAC

AACGGCGAGTATACCGTGGATGTGGCGGATAAAGGTTATACCCTGAAC

ATCAAATTTGCCGGTAAAGAGAAAACTCCTGAGGAGCCGAAAGAGGAG

GTTACCATTAAAGCCAATCTGATCTATGCCGACGGAAAAACCCAGACG

GCGGAGTTCAAAGGCACATTCGAAGAAGCAACTGCCGAAGCTTATCGT

TATGCTGATGCCCTGAAAAAAGACAATGGCGAGTATACGGTGGACGTT

GCCGACAAAGGCTATACGCTGAACATCAAATTCGCTGGTAAAGAGAAA

ACCCCAGAAGAACCAAAAGAGGAGGTTACGATCAAAGCCAACCTGATC

TATGCCGATGGGAAAACACAAACAGCTGAGTTCAAAGGGACGTTTGAG

GAGGCTACTGCTGAGGCCTATCGCTATGCCGACCTGCTGGCTAAAGAA

AACGGGAAATATACAGTCGATGTGGCCGACAAAGGTTATACGCTGAAC

ATCAAATTCGCCGGTAAAGAAAAAACACCGGAGGAGCCTAAAGAAGAA

GTCACCATCAAAGCCAACCTGATTTATGCCGACGGAAAAACACAAACT

GCCGAGTTCAAAGGAACGTTTGCCGAAGCGACGGCGGAAGCATATCGC

TATGCCGATCTGCTGGCCAAAGAGAACGGAAAATATACGGCCGACCTG

GAAGATGGAGGTTATACAATCAACATTCGTTTCGCCGGTAAAAAAGTG

GACGAGAAACCGGAAGAACCGATGGACACCTATAAACTGATTCTGAAC

GGAAAAACGCTGAAAGGCGAGACAACAACCGAAGCCGTGGACGCTGCT

ACTGCTGAAAAAGTGTTCAAACAATATGCCAACGACAACGGTGTGGAT

GGAGAATGGACCTATGACGATGCCACCAAAACATTCACAGTGACCGAG

AAACCAGAAGTCATTGACGCCTCGGAACTGACTCCGGCGGTTACAACA

TATAAACTGGTCATTAACGGAAAAACCCTGAAAGGCGAGACTACCACA

-continued

AAAGCGGTAGACGCTGAAACAGCGGAGAAAGCATTCAAACAATATGCC

AATGATAATGGCGTTGACGGCGTTTGGACATATGACGACGCTACGAAA

ACCTTCACGGTGACGGAAATGTAA

For the in situ orientation of the IgM isotype control, IgM-Cy5 (0.3 mg/mL) and GST-PpL (0.02 mg/mL) were diluted into GSH-B (100 mM GSH, 50 mM sodium borate, pH 8.5, and 0.5 mg/mL BSA). For comparison, IgM-Cy5 was printed alone in the standard print buffer (PB, 10 mM sodium phosphate, 15 mM sodium chloride, and 0.5 mg/mL BSA). The solutions were loaded into 384-well microtiter plates (Whatman, Piscataway, N.J.) and placed into the SpotBot 2 Personal Microarrayer (ArrayIt Corp., Sunnyvale, Calif.) using SMP3 pins (ArrayIt), which fabricate spots ~100 μm in area. The printing chamber was kept at a constant humidity of around 50% and the source plate was kept at 8° C. Prior to the print, a print file was generated using the MMF Spocle program. After the print was finished, the cold plate was turned off and the slides were incubated and warmed to room temperature over 2 hours. After 2 hours, the slides were placed into a coplin jar containing slide blocking buffer (50 mM ethanolamine in 100 mM sodium borate buffer, pH 8.5) and incubated at room temperature for 1 hour. Slides were then washed with PBS containing 0.05% Tween®-20 (0.05% PBS-T, 3×3 minutes) and then washed once with PBS. Slides were dried with a slide spinner (Labnet Intl., Edison, N.J.), and then affixed to a 24-well microarray gasket (ArrayIt). Slides were then hybridized with goat polyclonal α-μ chain DyLight 549 conjugated (1 μg/mL, 100 μL total volume, Abcam, ab98747) in 0.005% PBS-T and incubated at room temperature for 2 hours. After incubation, the wells were aspirated and washed with 0.005% PBS-T (3×3 minutes). The gaskets were then removed and the slides were placed into a coplin jar filled with PBS and washed for 3 minutes, dried using the slide spinner, and scanned using a Genepix 4100A slide scanner (Molecular Devices Corp., Union City, Calif.). Genepix Pro 5.1 software was used to extract data and Microsoft Excel software was used for statistical analysis and for generating tables and graphs. Error bars represent the standard deviation from the median values.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of directing in situ oriented immobilization of a protein on a support, said method comprising:
   providing a support;
   contacting the support with a solution comprising:
      a protein comprising a coupling moiety, wherein the protein is a recombinant fusion protein and the coupling moiety comprises glutathione-S-transferase (GST) and
      a glutathione molecule comprising a first group reactive with the support and a second group reactive with the coupling moiety,
   wherein the glutathione molecule binds (i) the support at the first group and (ii) the coupling moiety at the second group, thereby immobilizing and orienting, in situ, the protein on the support.

2. The method according to claim 1, wherein the support has a homogenous chemistry.

3. The method according to claim 1, wherein the support comprises N-Hydroxysuccinimide (NHS) or epoxide.

4. The method according to claim 1, wherein the solution has a pH of about 8.5.

5. The method according to claim 1, wherein the coupling moiety is located at the N-terminal region of the protein or the C-terminal of the protein.

6. The method according to claim 1, wherein the protein comprises lectin.

7. The method according to claim 6, wherein the protein is oriented to increase accessibility of a carbohydrate-binding site.

8. The method according to claim 1, wherein the support comprises glass or metal.

9. The method according to claim 1, wherein the protein comprises a polyhistidine tag.

10. The method according to claim 1, wherein said contacting is carried out by printing.

11. The method according to claim 1, wherein the solution further comprises an antibody to which the protein binds, and said method is carried out to direct in situ oriented immobilization of an antibody on a support.

12. The method according to claim 11, wherein the protein comprises Protein A (SpA), Protein G (SpG), or a fragment thereof.

13. The method according to claim 11, wherein the antibody is IgG, or a fragment thereof.

14. The method according to claim 11, wherein the protein binds the antibody via an Fc domain.

15. The method according to claim 11, wherein the protein is *Peptostreptococcus magnus* PpL.

16. The method according to claim 15, wherein the antibody is a multivalent antibody selected from IgM and IgA, or a fragment thereof.

17. The method according to claim 15, wherein the *Peptostreptococcus magnus* PpL binds the antibody at a light chain fragment of the antibody.

* * * * *